US008591947B2

(12) United States Patent
Vergez et al.

(10) Patent No.: US 8,591,947 B2
(45) Date of Patent: Nov. 26, 2013

(54) DUAL CONTROLLED RELEASE DOSAGE FORM

(71) Applicants: Juan A. Vergez, Buenos Aires (AR); Marcelo A. Ricci, Buenos Aires (AR)

(72) Inventors: Juan A. Vergez, Buenos Aires (AR); Marcelo A. Ricci, Buenos Aires (AR)

(73) Assignee: Osmotica Kereskedelmi és Szolgáltató KFT, Budapest (HU)

( * ) Notice: Subject to any disclaimer, the term of this patent is extended or adjusted under 35 U.S.C. 154(b) by 0 days.

(21) Appl. No.: 13/625,658

(22) Filed: Sep. 24, 2012

(65) Prior Publication Data

US 2013/0108693 A1   May 2, 2013

Related U.S. Application Data

(60) Continuation of application No. 11/355,315, filed on Feb. 15, 2006, now Pat. No. 8,329,217, which is a continuation-in-part of application No. 11/321,736, filed on Dec. 29, 2005, now Pat. No. 8,241,667, which is a division of application No. 09/992,488, filed on Nov. 6, 2001, now abandoned.

(51) Int. Cl.
*A61K 9/24* (2006.01)

(52) U.S. Cl.
USPC .......................................................... 424/473

(58) Field of Classification Search
None
See application file for complete search history.

(56) References Cited

U.S. PATENT DOCUMENTS

| | | | |
|---|---|---|---|
| 2,853,418 A | 9/1958 | Smith | |
| 3,184,836 A | 5/1965 | Stephenson | |
| 4,111,202 A | 9/1978 | Theeuwes | |
| 4,309,996 A | 1/1982 | Theeuwes | |
| 4,327,725 A | 5/1982 | Cortese | |
| 4,449,983 A * | 5/1984 | Cortese et al. | 604/892.1 |
| 4,455,143 A | 6/1984 | Theeuwes | |
| 4,612,008 A | 9/1986 | Wong | |
| 4,624,847 A | 11/1986 | Ayer | |
| 4,627,971 A | 12/1986 | Ayer | |
| 4,662,880 A | 5/1987 | Hamel | |
| 4,681,583 A | 7/1987 | Urquhart | |
| 4,723,957 A | 2/1988 | Magruder | |
| 4,765,989 A | 8/1988 | Wong | |
| 4,814,181 A | 3/1989 | Jordan | |
| 4,863,456 A | 9/1989 | Stephens | |
| 4,867,969 A | 9/1989 | Magruder | |
| 4,904,474 A | 2/1990 | Theeuwes | |
| 4,915,954 A | 4/1990 | Ayer | |
| 4,931,285 A | 6/1990 | Edgren | |
| 4,960,416 A | 10/1990 | Stephens | |
| 4,971,790 A | 11/1990 | Magruder | |
| 4,996,061 A | 2/1991 | Webb | |
| 5,006,346 A | 4/1991 | Edgren | |
| 5,082,668 A | 1/1992 | Wong | |
| 5,160,743 A | 11/1992 | Edgren | |
| 5,160,744 A | 11/1992 | Jao | |
| 5,190,765 A | 3/1993 | Jao | |
| 5,208,037 A | 5/1993 | Wright | |
| 5,236,689 A * | 8/1993 | Wong et al. | 424/473 |
| 5,252,338 A | 10/1993 | Jao | |
| 5,399,359 A | 3/1995 | Baichwal | |
| 5,543,155 A | 8/1996 | Fekete et al. | |
| 5,674,895 A | 10/1997 | Guittard | |
| 5,788,987 A | 8/1998 | Busetti | |
| 5,840,754 A | 11/1998 | Guittard | |
| 5,866,164 A | 2/1999 | Kuczynski | |
| 5,912,268 A | 6/1999 | Guittard | |
| 6,004,582 A | 12/1999 | Faour | |
| 6,106,864 A | 8/2000 | Dolan | |
| 6,207,191 B1 | 3/2001 | Crison | |
| 2002/0010216 A1 | 1/2002 | Rogosky et al. | |
| 2006/0177510 A1 | 8/2006 | Vergez | |
| 2006/0204578 A1 | 9/2006 | Vergez | |

FOREIGN PATENT DOCUMENTS

| | | |
|---|---|---|
| JP | 2646170 | 8/1997 |
| JP | 2665858 | 10/1997 |
| WO | 96/12477 | 5/1996 |
| WO | 97/18814 | 5/1997 |
| WO | 00/12069 | 3/2000 |
| WO | 00/18997 | 4/2000 |
| WO | 01/51036 | 7/2001 |

OTHER PUBLICATIONS

Santus (Osmotic drug delivery: a review of the patent literature. in J. Controlled Release (1995), 35, pp. 1-21).
Herbig (Asymmetric-membrane tablet coatings for osmotic drug delivery. in J. Controlled Release (1995), 35, pp. 127-136).
Dmochowski, R. et al., Advancements in Pharmacologic Management of the Overactive Bladder, Urology, Dec. 2000, vol. 56 (Supplement 6A), 41-49.
Appell, R.A. et al., Clinical Evaluation of a Sustained-Release Form of Oxybutynin (Ditropan SR) for the Treatment of Detrusor Hyperreflexia in Neuropathic Patients, Urodynamics Society Symposium Abstracts, 1990, 228.
Sirkia, T. et al., use of Hydrophilic Polymers to Control Drug Release from Press-Coated Oxybutynin Hydrochloride Tablets, S.T.P. Pharmacia Sci.,1993, 21, 3-8.
Nilsson, C. G. et al., Comparison of a 10-mg Controlled Release Oxybutynin Tablet with a 5-mg Oxybutynin Tablet in Urge Incontinent Patients, 1997, 16:533-542.

\* cited by examiner

*Primary Examiner* — David J Blanchard
*Assistant Examiner* — Tigabu Kassa
(74) *Attorney, Agent, or Firm* — Rick Matos; Innovar, L.L.C.

(57) ABSTRACT

A dosage form that provides a controlled release of at least two different active agents is provided. Particular embodiments include a dosage form that provides therapeutically effective levels of a first active agent and a second active agent in a mammal for an extended period of time following oral administration. An osmotic device containing a bi-layered core is provided. The osmotic device provides a dual controlled release of both drugs from the core. The layers of the core are in stacked, substantially concentric or substantially eccentric arrangement.

110 Claims, 3 Drawing Sheets

DUAL CONTROLLED RELEASE DOSAGE FORM

CROSS-REFERENCE TO EARLIER FILED APPLICATIONS

This application claims the benefit of and is continuation of U.S. Ser. No. 11/355,315, filed Feb. 15, 2006, now U.S. Pat. No. 8,329,217 issued Dec. 11, 2012, which is a continuation-in-part of U.S. application Ser. No. 11/321,736 filed Dec. 29, 2005, now U.S. Pat. No. 8,241,667 issued Aug. 14, 2012, which is a divisional of U.S. application Ser. No. 09/992,488 filed Nov. 6, 2001, now abandoned, the entire disclosures of which are hereby incorporated by reference.

FIELD OF THE INVENTION

This invention pertains to a dosage form that provides a controlled release of two different drugs. More particularly, it pertains to a coated dosage form having a bilayered core wherein each layer includes a respective drug that is released in a controlled manner.

BACKGROUND OF THE INVENTION

Osmotic devices and other tablet formulations are known for their ability to provide a controlled release of a wide range of drugs. Such osmotic devices and other tablet formulations are disclosed in U.S. Pat. No. 4,014,334 to Theeuwes et al., U.S. Pat. No. 4,576,604 to Guittard et al., Argentina Patent No. 234,493, U.S. Pat. No. 4,673,405 to Guittard et al., U.S. Pat. No. 5,558,879 to Chen et al., U.S. Pat. No. 4,810,502 to Ayer et al., U.S. Pat. No. 4,801,461 to Hamel et al., U.S. Pat. No. 5,681,584 to Savastano et al., U.S. Pat. No. 3,845,770 and Argentina Patent No. 199,301, the entire disclosures of which are hereby incorporated by reference.

Osmotic devices have demonstrated utility in delivering beneficial active agents, such as medicines, nutrients, food, pesticides, herbicides, germicides, algaecides, chemical reagents, and others, to an environment of use in a controlled manner over prolonged periods of time. Known devices include tablets, pills, and capsules.

Advancements in the art have focused on developing osmotic devices with improved semipermeable or porous membranes, various coatings surrounding the core and/or the semipermeable membrane, layered osmotically effective agents in the core of the device, specific release profiles for specific active substances, and specific membrane or core compositions.

U.S. Pat. No. 4,931,285, U.S. Pat. No. 5,006,346 and U.S. Pat. No. 5,160,743 to Edgren et al., U.S. Pat. No. 5,160,744, U.S. Pat. No. 5,190,765 and U.S. Pat. No. 5,252,338 to Jao et al., U.S. Pat. No. 4,612,008, U.S. Pat. No. 4,765,989 and U.S. Pat. No. 5,082,668 to Wong et al., U.S. Pat. No. 4,327,725 to Cortese et al., U.S. Pat. No. 5,208,037 to Wright et al., U.S. Pat. No. 4,904,474 to Theeuwes et al. and U.S. Pat. No. 4,627,971 to Ayer disclose osmotic devices comprising a bi-layered core surrounded by a semipermeable membrane having at least one hole (or passageway). The bi-layered core, however, comprises a first push-layer containing no drug and a second layer containing drug. The hole(s) can be placed anywhere along the semipermeable membrane. These patents do not disclose a core having two different drug-containing layers, each providing a controlled release of drug through a respective hole in the semipermeable membrane.

U.S. Pat. No. 5,543,155 to Fekete et al. discloses an osmotic device comprising a bi-layered core surrounded by a semipermeable membrane having two holes (or passageways). The bi-layered core, however, comprises a first push-layer containing no drug and a second layer containing drug. The hole(s) can be placed anywhere along the semipermeable membrane. This patent does not disclose a core having two different drug-containing layers, each providing a controlled release of drug through a respective hole in the semipermeable membrane.

U.S. Pat. No. 4,662,880 to Hamel et al., U.S. Pat. No. 4,723,957, U.S. Pat. No. 4,867,969 and U.S. Pat. No. 4,971,790 to Magruder et al. disclose osmotic devices comprising a single-layered core surrounded by a semipermeable membrane having two oppositely placed holes. A drug-containing coat further surrounds the semipermeable membrane. These patents do not disclose a core having two different drug-containing layers, each providing a controlled release of drug through a respective hole in the semipermeable membrane.

U.S. Pat. No. 4,624,847 to Ayer et al. discloses an osmotic device comprising a semipermeable membrane surrounding a compartment that houses a drug-containing polymer that increases in size and releases drug. The semipermeable membrane has two oppositely placed holes for releasing drug. This patent does not disclose an osmotic device comprising core having two different drug-containing layers, each providing a controlled release of drug through a respective hole in the semipermeable membrane.

U.S. Pat. No. 4,915,954 to Ayer et al. and U.S. Pat. No. 4,814,181 to Jordan et al. disclose an osmotic device having a bi-layered core surrounded by a semipermeable membrane. The first layer comprises a first drug that is released from the core rapidly over a period of 2 min to 2 hr. The second layer comprises a second drug that is released from the core at a controlled rate over a long period of time. The layers of the core are in intimate contact and are not separated by another layer, lamina or membrane. The semipermeable membrane can have two holes, one hole adjacent each of the two layers of the core such that each layer releases drug through its own respective hole. The Ayer et al. and Jordan et al. patents do not disclose an osmotic device having a bi-layered core, wherein the layers are in contact with each other and in laminar arrangement with respect to one another and wherein each layer provides a prolonged and controlled release of an active agent.

U.S. Pat. No. 4,455,143 to Theeuwes et al. discloses an osmotic device having two compartments defined by a surrounding semipermeable membrane and a partition between the compartments. The semipermeable membrane has two oppositely placed holes, one for each compartment. Each compartment contains a drug that is delivered at a controlled rate through a respective hole in the surrounding membrane. The partition is required and retains its integrity during operation of the osmotic device.

U.S. Pat. No. 5,866,164 to Kuczynski et al. of Alza Corporation discloses an osmotic device having a bi-layered core surrounded by a semipermeable membrane. There is no partition between the layers. The core includes a drug-containing layer and a push-layer; and passageways in the surrounding semipermeable membrane only communicate the drug-containing layer, and not the push-layer, to the exterior of the device. This osmotic device was specifically designed to release only the drug in the drug-containing layer and retain the drug in the push-layer.

While the prior art discloses a wide variety of osmotic devices, none of the prior art discloses an osmotic device that provides a controlled delivery of at least two different active agents, wherein: a) the core of the osmotic device is bi-layered and comprises a first pharmaceutical composition in laminar arrangement with a second pharmaceutical composition; b) the pharmaceutical compositions are in contact with one another; and c) drug is released from each layer through a passageway in a surrounding membrane (coat).

None of the prior art discloses an osmotic device comprising a dual layered core, wherein each layer of the core provides a controlled release of its respective drug and wherein the layers are in direct (intimate) contact, i.e., the layers are not separated by a partition or another layer, and wherein neither layer is required to be a push-layer, per se.

SUMMARY OF THE INVENTION

The present invention provides an oral dosage form that provides a controlled release device of two or more different active agents. The core of the osmotic device comprises a bi-layered core comprising two controlled release layers, wherein the two layers are in direct (intimate) contact with each other. They are not separated by another layer. Each layer comprises a respective pharmaceutical composition that provides a controlled release of a respective active agent. The core is surrounded by a membrane having at least one or two preformed holes. At least one hole in the membrane contacts the first layer of the core, and at least one hole in the membrane contacts the second layer of the core. The first pharmaceutical composition provides a controlled release of a first active agent through its respective first preformed passageway(s) in the semipermeable membrane. The second pharmaceutical composition provides a controlled release of a second active agent through a respective second passageway(s) in the semipermeable membrane. Both layers deliver their respective active agent through osmotic pumping. The first and second passageways can be located anywhere on their respective portions of the semipermeable membrane; however, the first and second passageways can oppose one another. In one embodiment, the dosage form includes a single preformed passageway through which both the first and second active agents are released. In another embodiment, the dosage form delivers their respective active agent through a combination of diffusion and osmotic pumping.

One aspect of the invention provides a dual controlled release osmotic device comprising:

a core comprising a first controlled release layer and a second controlled release layer, wherein the layers are in laminar arrangement and in direct or intimate contact with one another; and a semipermeable membrane surrounding the core, wherein the membrane comprises at least two preformed passageways, wherein at least one first passageway is in communication with the first layer and at least one second passageway is in communication with the second layer;

whereby the first layer provides a controlled release of a first active agent through the first passageway according to a first release profile and the second layer provides a controlled release of a different second active through the second passageway according to a second release profile.

Specific embodiments of the invention include those wherein: a) the release profile for the first active agent approximates the release profile of the second active agent; b) the release profile of the first active agent is different than the release profile of the second active agent; c) the first active agent is delivered to the upper to middle GI tract and the second active agent is delivered to the upper to lower GI tract of a mammal to which the dual osmotic device is delivered; d) the first and second active agents are delivered in a concurrent, sequential or overlapping manner; e) the first and second active are used to treat the same indication; f) the first active agent is delivered to the upper to middle GI tract and the second active agent is delivered to the middle to lower GI tract of a mammal to which the osmotic device is delivered; g) neither of the first or second layers is a "push-layer"; h) the first and second active agents are used to treat different signs and/or symptoms; and/or i) the first and the second active agents are used to treat the same signs and/or symptoms.

Another aspect of the invention provides a dual controlled release osmotic device comprising:

a core comprising a first active agent-containing controlled release layer and a second active agent-containing controlled release layer in contact with one another; and a semipermeable membrane surrounding the core, wherein the membrane comprises at least one preformed passageway in communication with at least one of the first and second active agent-containing layers;

whereby the osmotic device provides a controlled release of the first active agent through the at least one preformed passageway into a first environment of use according to a first release profile and the second layer provides a controlled release of the second active through the at least one preformed passageway into a second environment of use according to a second release profile.

Specific embodiments of the invention include those wherein: 1) the layers are in stacked arrangement; 2) the second active-agent containing layer surrounds the first active agent containing layer; 3) the osmotic device comprises at least one first preformed passageway in communication with the first active agent-containing layer and at least one second preformed passageway in communication with the second active agent-containing layer; 4) the membrane comprises at least one preformed passageway in communication with both the first and second active agent-containing layers; 5) the membrane comprises at least two preformed passageways and at least one of the two preformed passageways is plugged with a water soluble or water erodible material; 6) the membrane comprises at least two preformed passageways both of which are plugged with a water soluble or water erodible material, wherein the material plugging the first passageway may be the same as or different than the material plugging the second passageway; 7) the passageway(s) are plugged by the material comprising an external finish coat; 8) the osmotic device further comprises one or more coats interposed the semipermeable membrane and the core; 9) the osmotic device further comprises one or more coats external to the semipermeable membrane; 10) the osmotic device further comprises an external coat surrounding the membrane, and the membrane comprises at least a first preformed passageway and at least a second preformed passageway, wherein the first passageway has been formed after application of the external coat to the membrane, and the second passageway has been formed before application of the external coat to the membrane such that the second passageway is plugged by the external coat, and release of the second drug begins after release of the first drug has started 11) the osmotic device further comprises an external coat surrounding the membrane, and the membrane comprises at least a first preformed passageway and at least a second preformed passageway, wherein the first and second passageways have been formed before application of the external coat to the membrane; and the first and second passageways are plugged by the external coat; 12) the first and second active agents are the same; 13) the first and second active agents are different; 14) the external coat comprises one or more active agents that are the same as or different than the first and second active agents; 15) the first active agent has a first solubility in its environment of use and the second active agent has a different second water solubility in its environment of use; 16) the first and second environments of use are different; 17) the first active agent is more water soluble than the second active agent; 18) the second active agent is more water soluble than the first active agent; 19) the water solubility of the first and the second active agents are similar; and/or 20) the water solubility of the first and the second active agents are different.

Yet another aspect of the invention provides an osmotic device comprising:

a controlled release core comprising a first controlled release composition comprising a first drug and at least one pharmaceutical excipient, and a different second controlled release composition comprising a second drug and at least one pharmaceutical excipient, wherein the first and second compositions contact one another directly and are in stacked arrangement; and a membrane enveloping the core and having at least two passageways to permit release of the first and second drugs from the core when the osmotic device is exposed to an aqueous environment, wherein at least one first passageway is in communication with the first composition and at least one second passageway is in communication with the second composition.

Still another aspect of the invention provides an osmotic device comprising:

a core comprising a first controlled release composition comprising oxybutynin and at least one pharmaceutical excipient, and a different second controlled release composition comprising a second drug, selected from the group consisting of darifenacin, duloxetine and tolterodine, and at least one pharmaceutical excipient; and a semipermeable membrane enveloping the core and having at least two passageways to permit controlled release of oxybutynin and the second drug from the core when the osmotic device is exposed to an aqueous environment, wherein at least one passageway is in communication with the first composition and at least one passageway is in communication with the second composition.

Specific embodiments of the invention includes those wherein: 1) the osmotic device provides an oxybutynin release profile as described herein; 2) the osmotic device provides a second drug release profile as described herein; 3) the osmotic device provides an oxybutynin plasma concentration profile as described herein; and/or 4) the osmotic device provides a second drug plasma concentration profile as described herein.

Another aspect of the invention provides a coated dosage form comprising:

a core comprising oxybutynin, a second drug for treating incontinence and at least one pharmaceutical excipient, wherein the second drug is selected from the group consisting of darifenacin, duloxetine and tolterodine; and a wall enveloping the core.

Specific embodiments of the invention include those wherein: 1) the wall is microporous, permeable, semipermeable or impermeable; 2) the wall further comprises one or more preformed passageways to permit release of oxybutynin and the second drug when the dosage form is exposed to an aqueous environment; 3) the wall is a multi-layered wall comprising two or more laminas that are independently selected at each occurrence from inert and drug-containing; 4) the two or more laminas are independently selected at each occurrence from microporous, permeable, semipermeable and impermeable; and/or 5) the two or more laminas are independently selected at each occurrence from water soluble and water erodible.

A more specific aspect of the invention provides an osmotic device comprising:

a core comprising a first composition comprising oxybutynin and at least one pharmaceutical excipient, and a different second composition comprising a second drug, selected from the group consisting of darifenacin, duloxetine and tolterodine, and at least one pharmaceutical excipient, wherein the first and second compositions contact one another and are in stacked arrangement; and a semipermeable membrane enveloping the core and having at least two passageways to permit controlled release of oxybutynin and the second drug from the core when the osmotic device is exposed to an aqueous environment, wherein at least one passageway is in communication with the first composition and at least one passageway is in communication with the second composition;

wherein, when the osmotic device is exposed to an aqueous environment, oxybutynin is released according to a release profile as described herein.

Other specific embodiments of the invention include those wherein: 1) the osmotic device provides a single dose plasma level for darifenacin is sufficient to provide a desired therapeutic response in a subject; 2) the osmotic device provides a single dose plasma level for oxybutynin in the range of about 4-7 or 1-10 ng per ml of plasma; 3) the osmotic device provides a single dose plasma level for tolterodine in the range of about 0.5-25 ng per ml of plasma; 4) the osmotic device comprises a finish coat exterior to the semipermeable membrane; or 5) the osmotic device provides a single dose plasma level for duloxetine sufficient to provide a desired therapeutic response in a subject.

The invention also provides a therapeutic device for the delivery of pharmaceutically active agents, ranging in solubility from slightly soluble to very soluble drugs, in a controlled, continuous and approximately steady, preferably zero order or pseudo-zero order, rate over a prolonged period of time. Depending upon the excipients used, among other things, the osmotic device can also deliver drugs according to first order or pseudo-first order, release profiles. In addition, the osmotic device may provide targeted delivery of a drug.

The device of the present invention is optionally provided with an external coating disposed on the outside of the osmotic device and comprising one or more active agents for immediate delivery to the environment of use. The external coating can contain a loading dose of an active agent in the core of the device.

Other features, advantages and embodiments of the invention will become apparent to those of ordinary skill in the art by the following description, accompanying examples and appended claims.

BRIEF DESCRIPTION OF THE FIGURES

The following drawings are part of the present specification and are included to further demonstrate certain aspects of the invention. The invention may be better understood by reference to one or more of these drawings in combination with the detailed description of the specific embodiments presented herein.

FIG. 9 depicts a sectional side view of a fifth alternate delivery device.

FIG. 10 depicts a sectional side view of a sixth alternate delivery device.

FIG. 11 depicts a sectional side view of a seventh alternate delivery device.

DETAILED DESCRIPTION OF THE INVENTION

Figure 1:
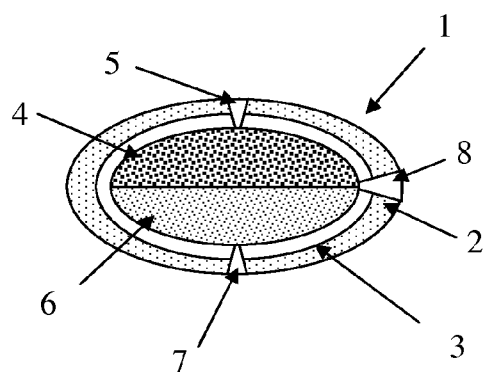
FIG. 1 depicts a sectional side view of a delivery device according to the present invention.

The dosage forms of the invention will release each drug independently according to a controlled, sustained, slow, timed, targeted, pseudo-first order, first order, pseudo-zero order, zero-order and/or delayed release profile. The particular release profiles for the first active agent and the second active agent in a particular dosage form will depend upon the specific combination of first active agent and second active agent present and the excipients used to make the dosage form. For example, a dosage form might provide: 1) a controlled release of the first drug and a controlled release of the second drug; 2) a sustained delivery of the first drug and of the second drug for about one day or a period of about 18-26 hours, and preferably about 24 hours; 3) a controlled and delayed release of the first drug and a controlled but not substantially delayed release of the second drug; 4) a controlled and delayed release of the second drug and a controlled but not substantially delayed release of the first drug; 5) a release profile for the first active agent approximating the release profile of the second active agent; 7) a release profile of the first active agent different than the release profile of the second active agent and/or 8) a concurrent, sequential or overlapping release of the first and second active agents.

The first and second active agents can be formulated as pharmaceutically acceptable salts. As used herein, "pharmaceutically acceptable salts" refer to derivatives of the disclosed compounds, wherein the therapeutic compound is modified by making acid or base salts thereof. Examples of pharmaceutically acceptable salts include, but are not limited to, mineral or organic acid salts of oxybutynin. The pharmaceutically acceptable salts include the conventional non-toxic salts, for example, from non-toxic inorganic or organic acids. For example, such conventional non-toxic salts include those derived from inorganic acids such as hydrochloric, hydrobromic, sulfuric, sulfonic, sulfamic, phosphoric, nitric and the like; and the salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and others known to those of ordinary skill in the art. For acidic compounds, the salt may include an amine-based (primary, secondary, tertiary or quaternary amine) counter ion, an alkali metal cation, or a metal cation. Lists of suitable salts are found in texts such as *Remington's Pharmaceutical Sciences*, 18th Ed. (Alfonso R. Gennaro, ed.; Mack Publishing Company, Easton, Pa., 1990); *Remington: the Science and Practice of Pharmacy* 19th Ed.(Lippincott, Williams & Wilkins, 1995); *Handbook of Pharmaceutical Excipients*, 3rd Ed. (Arthur H. Kibbe, ed.; Amer. Pharmaceutical Assoc., 1999); the *Pharmaceutical Codex: Principles and Practice of Pharmaceutics* 12th Ed. (Walter Lund ed.; Pharmaceutical Press, London, 1994); The United States Pharmacopeia: The National Formulary (United States Pharmacopeial Convention); and *Goodman and Gilman's: the Pharmacological Basis of Therapeutics* (Louis S. Goodman and Lee E. Limbird, eds.; McGraw Hill, 1992), the disclosures of which are hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The tablet dosage forms useful in the present invention include, by way of example and without limitation, pressed tablets, layered tablets, osmotic device tablets, coated tablets, enteric coated tablets, centered tablets (tablets containing another tablet inside), prolonged release tablets, slow release tablets and molded tablets.

FIG. 1 depicts a controlled release dosage form (1) including a bi-layered core, wherein the first active agent-containing layer (4) is in laminar (stacked) arrangement with respect to the second active agent-containing layer (6). The core is enveloped by a wall (3) having at least two preformed passageways (5, 7). The passageway (5) is in communication with the first active agent-containing layer (4), and the passageway (7) is in communication with the second active agent-containing layer (6). The dosage form also includes an optional external coat (2). As depicted in this exemplary embodiment, the passageways (5,7) is made after the external coat (2) is placed onto the wall (3).

The wall (3) can be microporous, permeable, impermeable or semipermeable. By "microporous" is meant a membrane that permits release of the active agent in the core by diffusion through micropores or pores in a surrounding membrane. By "permeable" is meant that the wall permits passage of fluid and of ingredient(s). By "impermeable" is meant that the wall does not permit passage of any fluid or ingredient(s). By semipermeable membrane is meant a membrane that permits the influx of a liquid from the exterior of the delivery device to the interior of the delivery device, while at the same allowing release of the active agent in the core by osmotic pumping through the preformed passageway in the semipermeable membrane. The wall can maintain or lose its physical integrity during use. The permeability and physical stability of the wall depend upon the materials used to make the wall.

The external coat (2) is optional and can be inert, i.e., excluding any active agent, or can contain one or more active agents, e.g., a drug-containing coat. The external coat can maintain or lose its physical integrity during use, i.e., the coat can be water soluble or water erodible. The physical stability of the wall depends upon the materials used to make the wall. If the external coat contains an active agent, the release rate of the active agent can be rapid, immediate, controlled, delayed, slow, sustained, timed, or targeted. The external coat can also include a loading dose of the first and/or second active agents in the core of the dosage form.

The core releases the first and second active agents; however, the rate of release of each is determined by the composition of the layer in which each is found, the composition of the wall (3) and the composition of the optional external coat (2). For example, when the wall (3) is a semipermeable or impermeable wall, the dosage form will provide a controlled release of both active agents. When the wall (3) is permeable or microporous, the dosage form will provide a more rapid and less controlled release of both active agents. Generally, the release rate of the active agents from the core increases as the permeability of the wall (3) increases.

Unlike other known osmotic devices, the layers of the core in the osmotic device (1) can be adjacent and in intimate contact with one another. Each layer (4,6) releases its drug at a controlled rate. Surprisingly, the osmotic device does not require a push-layer, i.e., a layer that absorbs water and expands, in order to release drug from each layer or from the opposing surfaces of the osmotic device. Also, the osmotic device unexpectedly does not require a partition between the layers (4,6) of the core in order to release drug from each layer or from the opposing surfaces of the osmotic device.

Exemplary formulations for the dosage form (1) are detailed in Examples 1 and 2, wherein the dosage form is an osmotic device and includes an inert water soluble or erodible external coat (2) that does not contain drug. The osmotic device of Example 1 includes two different compositions in the core, which is surrounded by a semipermeable membrane. The first composition comprises oxybutynin, whereas the second composition comprises tolterodine. When this osmotic device is placed in an aqueous environment, it provides a controlled release of oxybutynin and tolterodine.

The dosage form (1) can also include: a) the external coat (2) as a drug-containing coat that contains oxybutynin and a second drug in rapid or immediate release form; b) the wall (3) as a water soluble or erodible coat; and c) a core as a controlled, slow, or sustained release core that contains the active agents. Although the core is depicted in each of FIGS. 1-5 as a bi-layered (stacked arrangement) core, the invention includes embodiments wherein the core is comprised of concentric lamina such that the first active agent is in a central inner core and the second active agent is in a lamina surrounding the inner core (see FIGS. 9-10).

The passageway of the device (1) can be in communication with both layers of the core. The passageway (8) extends through the external coat (2) and the wall (3) and communicates the exterior of the device to both compositions (4, 6) in the core. By using this type of construction, the device can deliver both active agents simultaneously through a single passageway.

The relative amounts of each active agent released at a given time can be controlled by changing the location of the passageway(s) in the wall (3). For example, if the first (4) and second (6) compositions have the same release properties and the device includes the sole passageway (5) centered on the composition (4), the device (1) will release a major portion of the first composition (4) before it releases any of the composition (6). If the first (4) and second (6) compositions have the same release properties and the device includes the sole passageway (5) in communication with the composition (4) and proximal but not in direct communication with the composition (6), the device (1) will release only a minor portion of the first composition (4) by the time it begins to release the second composition (6).

The relative amounts of each active agent released at a given time can be controlled by using compositions that provide predetermined release profiles. For example, if each composition (4, 6) has its own passageway (5, 7, respectively) located as depicted in FIG. 1, the device will provide a faster release of the drug in composition (4) if the composition (4) possesses a twelve-hour controlled release profile and the composition (6) possesses a twenty four-hour controlled release profile. Neither one of the compositions in the core is intended for rapid release of active agent.

Where the composition (4) includes an enteric release polymer and the composition (6) does not, the device (1) can provide a delayed and controlled release of the drug in the composition (4) and a controlled but not substantially delayed release of the drug in the composition (6).

Figure 2:
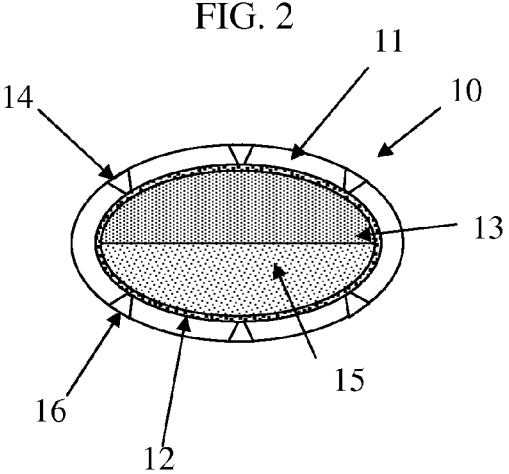
FIG. 2 depicts a sectional side view of an alternate delivery device according to the present invention.

FIG. 2 depicts an alternate embodiment of a controlled release dosage form according to the invention. The dosage form (10) includes a core comprising a first composition (13) in stacked arrangement with a second composition (15), wherein the core is enveloped by an internal coat (12) and then by a wall (11). The first composition (13) comprises a first active agent and the second composition (15) comprises a second active agent. The internal coat (12) can be an inert, release rate controlling, enteric, microporous, permeable, semipermeable, delayed release, water soluble, or water erodible coat. The wall (11) can be a microporous, impermeable, semipermeable or impermeable wall. The internal coat (12) and wall (11) have different compositions. The wall (11) includes plural passageways (14, 16). The passageways (14) permit release of the first active agent from the core. The passageways (16) permit release of the second active agent from the core. In one embodiment, the wall is a semipermeable wall, the internal coat is an inert water soluble or water erodible coat, and the dosage form provides a concurrent controlled release of the first and second active agents. Although not depicted in FIG. 2, the passageways (14, 16) can extend through the wall (11) and the internal coat (12).

When the internal coat (12) is a release rate-controlling coat, it will control the rate of release of the first and second active agents. When the internal coat (12) is an enteric release coat, it will delay release of the active agents until the dosage form has reached the portion of the gastrointestinal tract downstream of the stomach, e.g, the ileum, duodenum, jejunum, intestines, colon and/or rectum. When the internal coat (12) is a microporous coat it will control release of the drugs from the core in a manner dependent upon the porosity of the coat, such that the rate of drug release increases as the porosity of the microporous coat increases. Neither of the first or second active agents is released rapidly from the core.

As depicted, the passageways (14, 16) are not blocked by a water soluble or water erodible material, since no additional material is coated onto the wall (11) after the passageways are drilled.

Figure 3:
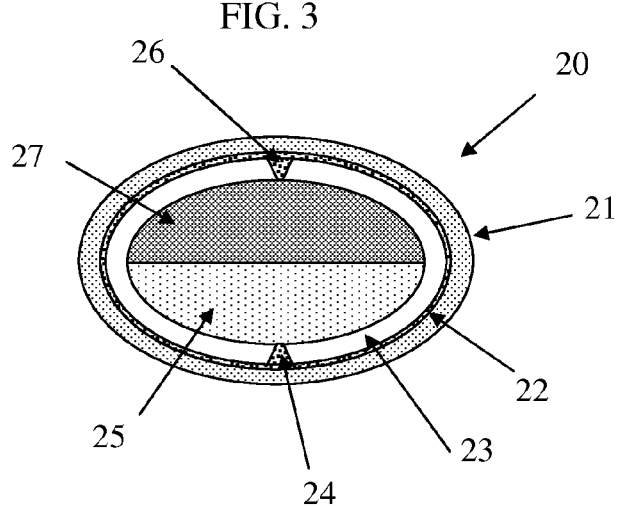
FIG. 3 depicts a sectional side view of a second alternate delivery device.

FIG. 3 depicts a controlled release dosage form (20) that includes a bi-layered core having first (27) and second (25) drug-containing layers. The core is surrounded by a wall (23), which is then surrounded by an inert internal coat (22) that does not contain drug. The external drug-containing or inert coat (21) surrounds the internal coat. The internal coat (22) is similar to and can include the same features of the internal coat (12) of the dosage form (10). The external coat (21) is similar to and can include the same features of the external coat (2) of the dosage form (1). The dosage form (20) provides a controlled release of first active agent through the passageway(s) (26) and a controlled release of the second active agent through the passageway(s) (24).

The passageways (24,26) are plugged by the same material used to form the internal coat (22), since the internal coat is applied to the wall (23) after the passageways are drilled through the wall (23).

When the external coat (21) contains one or more drugs and the coat (22) is inert and water soluble and/or water erodible, the dosage form will provide a delayed release of both drugs from the core. The length of the delay may be as short as one minute or as long as several to many hours. For example, the delay may be 0.5-5.0 hours or 1.0-3.0 hours.

Figure 4:
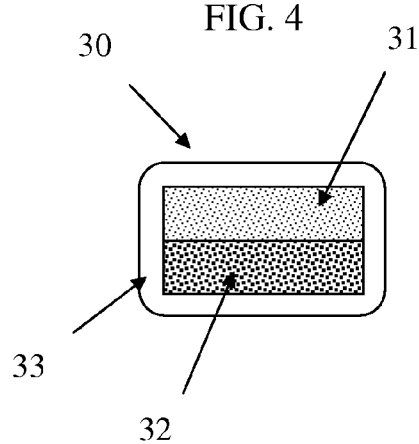
FIG. 4 depicts a sectional side view of a third alternate delivery device.

FIG. 4 depicts a bi-layered tablet (30) comprising a first composition (31) and a different second composition (32), wherein the tablet includes an external coat (33). The coat (33) can be similar to and can include the same features of the external coat (2) or (21), the internal coat (12) or (22) or the wall (3), (11) or (23). Accordingly, the dosage form (30) can provide controlled, sustained, slow or extended release of the active agents, optionally in a delayed or enteric release form.

The wall (33) can be a multi-layered wall comprising two or more lamina. At each occurrence, a lamina can be water soluble or water erodible and/or permeable, semipermeable, impermeable or microporous and/or inert or drug-containing. The wall can comprise one to six laminas.

Figure 5:
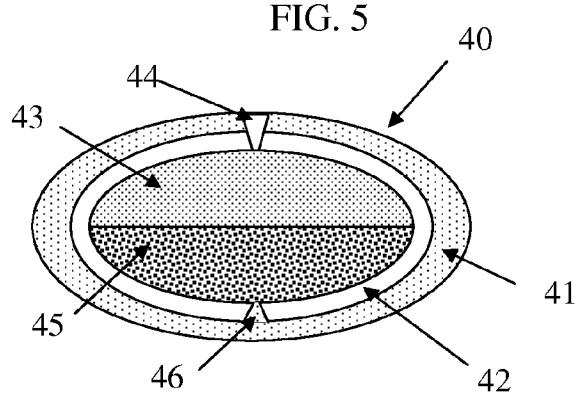
FIG. 5 depicts a sectional side view of a fourth alternate delivery device.

FIG. 5 depicts an osmotic device (40) comprising a bi-layered core surrounded by a semipermeable membrane (42), which is then surrounded by a drug-containing external coat (41). The osmotic device has two different types of preformed passageways. The passageway(s) (44), which communicates the drug-containing layer (43) of the core to the exterior of the device, is formed after the external coat is applied to the semipermeable membrane. The passageway(s) (46) is formed before the external coat is applied to the semipermeable membrane. Accordingly, the passageway(s) (46) is (are) plugged by the same material used to form the external coat (41). By virtue of its construction, this device will begin to release active agent from the layer (43) before it begins to release active agent from the layer (45). The delay period in the release of active agent from the layer (45) is related to the amount of time it takes for the external coat (41) to dissolve or erode: the longer it takes to dissolve or erode, the longer the delay period for release of active agent from the layer (45) through the passageway (46). The osmotic device (40), therefore, provides a controlled release of active agent from the layer (43), wherein release begins shortly after exposure of the device to an environment of use, and a delayed and controlled release of active agent from the layer (45), wherein release begins after release from the layer (43) has already begun.

FIGS. 9 and 10 depict embodiments of the controlled release dosage form wherein the layers of the core are substantially concentric. The dosage form (50) comprises a membrane (51) surrounding a bi-layered core. The core comprises an inner nucleus (53), comprising a first active agent, and a second layer (52) encircling the inner nucleus and comprising a different second active agent. The nucleus can be any shape. The preformed passageway passes through the membrane and is in contact with the nucleus The embodiment of FIG. 9 is particularly suited to provide a slightly delayed release of the second active agent. The geometry (shape) of the first and second compositions and/or the particular combination of excipients used can be modified to produce particular release profiles of each active agent.

The dosage form (55) also comprises a membrane (56) surrounding a bi-layered core. The core comprises an inner nucleus (58), comprising a first active agent, and a second layer (57) surrounding (enveloping) the inner nucleus and comprising a different second active agent. The nucleus can be any shape. The preformed passageway passes through the membrane and is in contact with the second composition (57). The embodiment of FIG. 10 is particularly suited to provide a moderately to substantially delayed release of the first active agent.

FIG. 11 depicts an embodiment of the dosage form wherein the first and second compositions are in stacked arrangement; however, their geometry has been modified to effect a particular release of each drug. For example, the surface between the two compositions is not flat as it is in the other embodiments.

In the embodiments of the invention that include more than one preformed passageway, the amount of each active agent released from each passageway can vary over time. For example, the dosage form (1) of FIG. 1 will initially release the first active agent composition (4) from its respectively adjacent passageway (5) and the second active agent composition (6) from its respectively adjacent passageway (7). However, after a period of time of exposure to an environment of use, portions of the core no longer contact the surrounding membrane (3) due to erosion and/or dissolution of the core at its surface. As a result, fluid that accumulates between the core and the membrane in the contains both the first and second active agents. Therefore, amounts of each drug can be released from each passageway. On the other hand, the dosage form (55) of FIG. 10 provides a completely different behavior. In this case, the first active agent composition (58) is released in a delayed manner only after a substantial portion of the second active agent composition (57) has been released. This is because the second active agent composition is exposed to fluid first and is immediately adjacent a passageway, whereas the first active agent composition is exposed to fluid later and is spaced away from the passageway. The dosage form (55) can thus be considered a delayed, timed, targeted, enteric or colonic release system that does not require recognized pH dependent enteric release or colonic release polymers in order to provide an enteric or colonic release of the first active agent composition.

Oxybutynin is commercially available as the free base or in its hydrochloride salt form from Abbott Laboratories Pharmaceutical Division (United States of America), Seloc AG (France), Sifa Ltd, (Ireland), Orgamol SA, Synkem Div. Plasto SA, Cedex (France), Gruppo Lepetit SA, Garessio (Italy) and Juzen Chemical Co. Ltd. The invention provides for the administration of oxybutynin in its free base, racemic, optically enriched, optically pure (R)- or (S)-, and/or pharmaceutically acceptable salt forms. The optically pure and optically enriched forms of oxybutynin are available from Sepracor (United States of America). The oxybutynin can also be included in a prodrug form or metabolite form (desethyloxybutynin). Unless otherwise specified, the term oxybutynin refers to all of the above-described forms of oxybutynin.

Oxybutynin is available in controlled release osmotic device tablet dosage forms called DITROPAN™ XL from Alza Corporation (Palo Alto, Calif.) and called DITROPAN™ UD from Osmodex (Buenos Aires, Argentina) and as a non-osmotic device tablet dosage form called CYSTRIN™ CR from Leiras OY (Finland). Oxybutynin is released from these tablet dosage forms at a controlled rate over a period of about 24 hours. Controlled release dosage forms of oxybutynin can also be manufactured according to the U.S. and foreign patents and patent applications incorporated herein by reference, and in particular according to U.S. Pat. No. 5,399,359, U.S. Pat. No. 5,912,268, U.S. Pat. No. 5,840,754, and U.S. Pat. No. 5,674,895, Japanese Patent Applications Serial No. 9,388 and U.S. Pat. No. 163,901. Controlled release dosage forms containing oxybutynin can also be prepared according to Nilsson et al. (*Neurourol. Urodyn.* (1997), 16 (6), pg. 533-42), International Publications No. WO 95/23,593, and No. WO 96/12,477 and U.S. Pat. No. 5,368,861, the entire disclosures of which are hereby incorporated by reference. These dosage forms would have to be modified according to the present invention to include a second drug in a separate composition for treating incontinence. Controlled release dosage forms can also be manufactured according to the examples herein.

Useful drugs suitable for the treatment of incontinence include darifenacin, tolterodine, amitryptyline, atropine, propantheline, imipramine, terodiline, dicyclomine, flurbiprofen, nitroflurbiprofen (HCT-1026), hyoscyamine, trospium, duloxetine, resiniferatoxin, desmopressin, propiverine, midodrine, glycopyrrolate, KRP-197, and others known to those of ordinary skill in the art. Other drugs suitable for the treatment of incontinence also include the histamine and serotonin compounds as disclosed in U.S. Pat. No. 5,877,198; the 1,2-diamino derivatives of cyclobutene 3-4 diones of U.S. Pat. No. 5,506,252, eg., (R)-4-[3,4-dioxo-2-(1,2,2-trimethyl-propylamino)-cyclobut-1-enylamino]-3-ethyl-benzonitrile; the pyrrole derivatives of U.S. Pat. No. 6,172,102; the 4,5-diamino derivatives of (1H)-pyrazoles of U.S. Pat. No. 6,172,222; the selective vasopressin V2 agonists of U.S. Pat. No. 6,194,407; the (+)-venlafaxine derivatives of U.S. Pat. No. 6,197,828; the enantiomerically enriched (R,R)-glycopyrrolate as disclosed in U.S. Pat. No. 6,204,285; the enantiomerically enriched (R)-trihexyphenidyl as disclosed in U.S. Pat. No. 6,207,681; the substituted esters, amides and ketones having smooth muscle relaxing properties of U.S. Pat. No. 6,207,852; the tropone derivatives of U.S. Pat. No. 6,221,868; the $_{1L}$-adrenoceptor agonist compounds disclosed in U.S. Pat. No. 6,268,389, e.g., 2-(3-dimethylamino-2-methylphenylimino)-imidazolidine; 2-(6-bromo-3-dimethylamino-2-methylphenylimino)imidazolidine; 2-(5-amino-2-chloro-4-dimethylamino-2-methylphenylimino)imidazolidine; 2-(2-chloro-5-trifluoromethylphenylamino)imidazolidine, 2-(3-amino-2-methylphenylimino)-imidazolidine, 2-(6-chloro-3-dimethylamino-2-methylphenylimino)imidazolidine and tiamenidine; the tricyclic pyridine N-oxides of U.S. Pat. No. 6,235,900; the compounds 4-[(2-tert-butylamino-3,4-dioxo-cyclobut-1-enylamino)-methyl]-3-chloro-benzonitrile and 3-(2,3-dichloro-6-methyl-benzylamino)-4-(1,1-dimethyl-propylamino)-cyclobut-3-ene-1,2-dione disclosed in PCT International Publication No. WO 98/11888; the analogs of glutamic acid and gamma-aminobutyric acid disclosed in PCT International Publication No. WO 00/61135; the 1-amino ethylindole derivatives disclosed in PCT International Publication No. WO 00/61554; the quinolinomorphinan derivatives disclosed in PCT International Publication No. WO 01/05795; the compounds 5-(2-ethyl-2Htetrazol-5-yl)-1,2,3,6-tetrahydropyridine, 5-(2-ethyl-2H-tetrazol-5-yl)-1-methyl-1,2,3,6-tetrahydropyridine as disclosed in PCT International Publication No. WO 01/13918; the compounds (+)-tramadol, O-demethyl-tramadol, (+)-O-demethyltramadol, O-desmethyl-N-mono-desmethyl-tramadol, (+)-O-desmethyl-N-mono-desmethyl-tramadol as disclosed in PCT International Publication No. WO 01/24783, and the quinolinoisoquinoline derivatives disclosed in PCT International Publication No. WO 01/40225. Still other suitable drugs for the treatment of incontinence are disclosed in PCT International Publications No. WO 98/09948, No. WO 99/52856, No. WO 00/02846, No. WO 01/02406, No. WO 01/27104, No. WO 01/36375, No. WO 01/36418, No. WO 01/47503, No. WO 01/600352. Additional suitable drugs for the treatment of incontinence are disclosed in U.S. Pat. No. 6,159,998, No. 6,172,041, U.S. Pat. No. 6,194,447, U.S. Pat. No. 6,218,404, and U.S. Pat. No. 6,248,549, the entire disclosures of which are hereby incorporated by reference. These drugs may be included as the second drug in the present pharmaceutical composition. Preferred second drugs include darifenacin and tolterodine.

Darifenacin can be used for treating irritable bowel syndrome and urinary incontinence. Darifenacin can be made according to the procedure described by Pfizer (European Patent No. 388,054 (1990) or Graul et al (*J. Drugs Future* (1996), 21 (11), 1105-1108). Darifenacin is available in the (R)-, (S)-, optically enriched and racemic form as well as the free-base or salt form. The darifenacin can also be included in a prodrug form or metabolite form. Unless otherwise specified, the term darifenacin refers to all of the above-described forms of darifenacin. Darifenacin is generally administered at a dose of 5-75 mg daily.

Tolterodine can be made according to the procedure described by KabiVitrum (European Patent No. 325,571 (1989)) or Andersson et al. (*J. O. C.* (1998), 63, 8067-8070). Tolterodine is available in the (R)-, (S)-, optically enriched and racemic form as well as the free-base or salt form. The tolterodine can also be included in a prodrug form or metabolite form (such as PNU-200577; (R)—N,N-diisopropyl-3-(2-hydroxy-5-hydroxymethylphenyl)-3-phenylpropylamine). Unless otherwise specified, the term tolterodine refers to all of the above-described forms of tolterodine. Tolterodine is generally administered at a dose of 2 to 4 or 0.5 to 5 mg daily.

Osmotic device formulations containing oxybutynin (2.5, 5 and 10 mg strength) and tolterodine (1 and 2 mg strength) are described in Example 1. The oxybutynin and the tolterodine are located in separate stacked layers in the core of the osmotic device.

Figure 6:
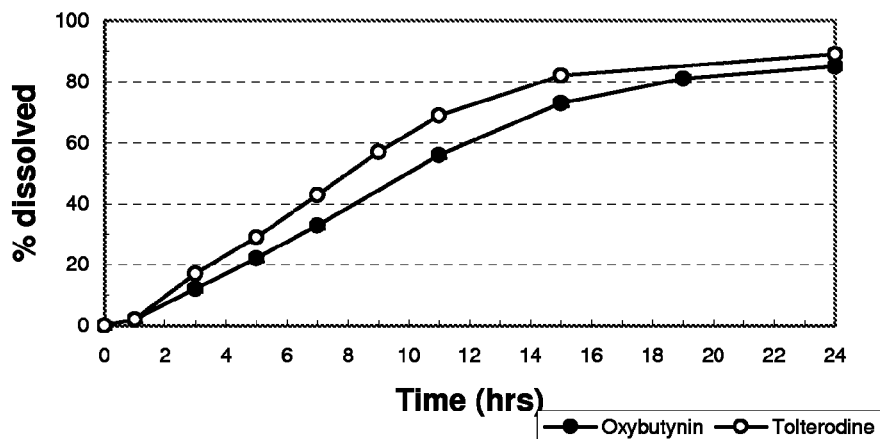
FIG. 6 depicts an in vitro release profile for oxybutynin and tolterodine as they are released from the osmotic device of Example 1.

FIG. 6 includes a dissolution profile for oxybutynin and tolterodine as they are released from the osmotic device of Example 1. The dissolution data is obtained in a paddle apparatus (USP type 2) operated at 100 rpm using distilled water at 37° C. as dissolution medium. The oxybutynin and tolterodine release profiles of the formulation of Example 1 are generally described as follows:

| | Oxybutynin Released | | | Tolterodine Released | | |
| --- | --- | --- | --- | --- | --- | --- |
| | | Range (%) | | | Range (%) | |
| Time (hs) | Average (%) | Min | Max | Average (%) | Min | Max |
| 1 | 2 | 0 | 10 | 3 | 0 | 12 |
| 3 | 12 | 5 | 25 | 17 | 3 | 25 |
| 5 | 22 | 17 | 36 | 29 | 17 | 36 |
| 7 | 33 | 20 | 50 | 43 | 31 | 50 |
| 9 | — | — | — | 57 | 49 | 66 |
| 11 | 56 | 40 | 70 | 69 | 61 | 76 |
| 15 | 73 | 58 | 84 | 82 | 74 | 90 |
| 19 | 81 | 70 | 89 | — | — | — |
| 24 | 85 | 76 | 100 | 89 | 76 | 100 |

The dissolution profiles for oxybutynin and tolterodine approximate one another; however, the tolterodine has a slightly faster rate of release. Although not shown in FIG. 6, the tolterodine can be made to achieve approximately complete dissolution at about 16 hours, and the oxybutynin can be made to achieve approximately complete dissolution at about 20 hours.

Figure 7:
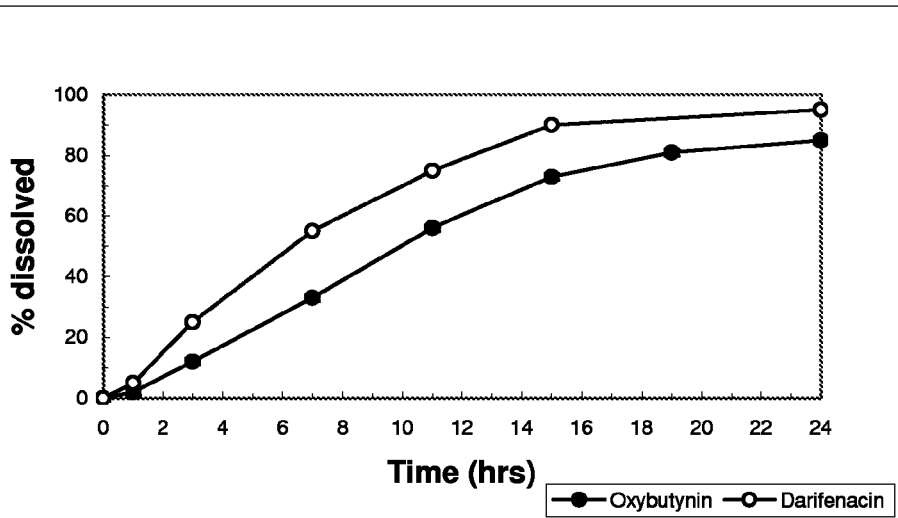
FIG. 7 depicts an in vitro release profile for oxybutynin and darifenacin as they are released from the osmotic device of Example 2.

Osmotic device formulations containing oxybutynin (5 and 10 mg strength) and darifenacin (5 and 10 mg strength) are described in Example 2. The oxybutynin and the darifenacin are located in separate stacked layers in the core of the osmotic device. FIG. 7 includes a dissolution profile for oxybutynin and darifenacin as they are released from the osmotic device of Example 2. The dissolution data is obtained in a paddle apparatus (USP type 2) operated as indicated above.

The oxybutynin and darifenacin release profiles of the formulation of Example 2 are generally described as follows:

|  | Oxybutynin Released | | | Darifenacin Released | | |
| --- | --- | --- | --- | --- | --- | --- |
|  | Average | Range (%) | | Average | Range (%) | |
| Time (hrs) | (%) | Min | Max | (%) | Min | Max |
| 1 | 2 | 0 | 10 | 5 | 0 | 12 |
| 3 | 12 | 5 | 25 | 25 | 10 | 35 |
| 7 | 33 | 20 | 50 | 55 | 25 | 65 |
| 11 | 56 | 40 | 70 | 75 | 45 | 89 |
| 15 | 73 | 58 | 84 | 90 | 74 | 98 |
| 19 | 81 | 70 | 89 | — | — | — |
| 24 | 85 | 76 | 100 | 95 | 89 | 100 |

The darifenacin has a slightly faster rate of release. Although not shown in FIG. 7, the darifenacin can be made to achieve approximately complete dissolution at about 18 hours, and the oxybutynin can be made to achieve approximately complete dissolution at about 22 hours.

Osmotic device formulations containing oxybutynin (5 and 10 mg strength) and darifenacin (5 and 10 mg strength) are described in Example 4. The oxybutynin and the darifenacin are located in separate stacked layers in the core of the osmotic device.

Figure 8:
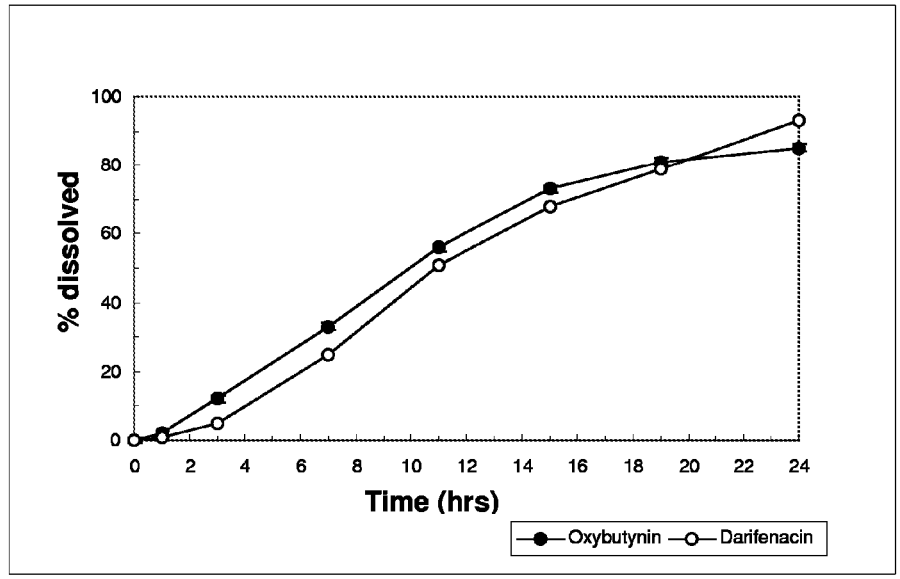
FIG. 8 depicts an in vitro release profile for oxybutynin and darifenacin as they are released from the osmotic device of Example 12.
Figure 8:
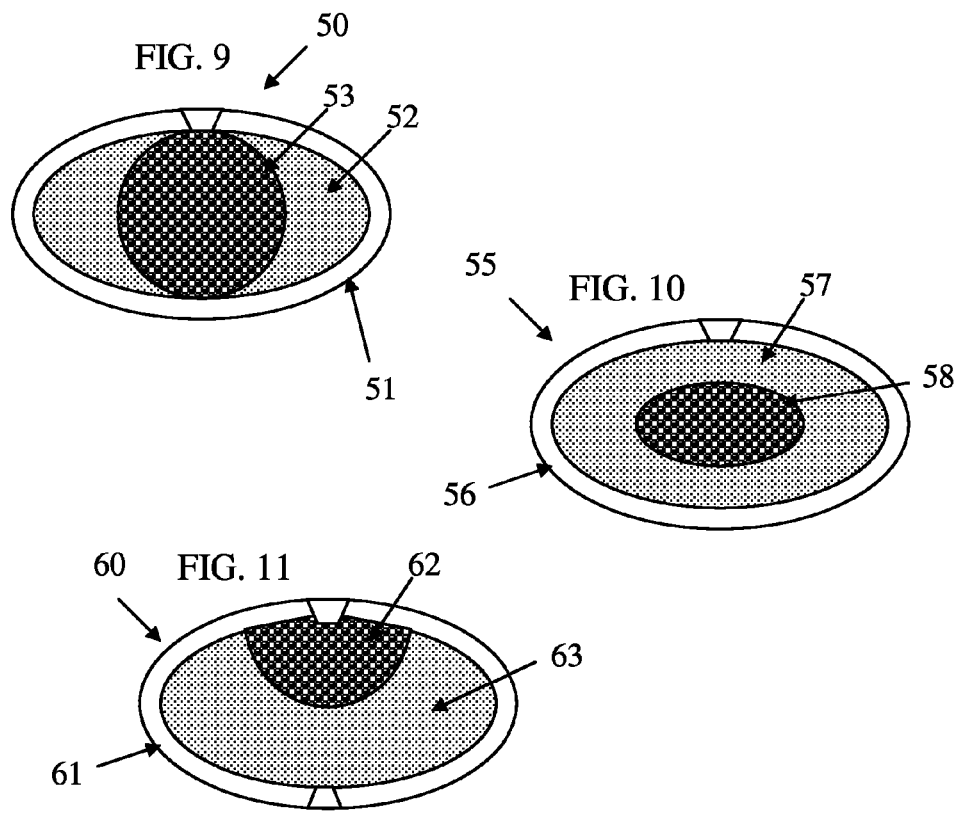

FIG. 8 includes a dissolution profile for oxybutynin and darifenacin as they are released from the osmotic device of Example 4. The dissolution data is obtained in a paddle apparatus (USP type 2) operated as indicated above. The oxybutynin and darifenacin release profiles of the formulation of Example 4 are generally described as follows:

|  | Oxybutynin Released | | | Darifenacin Released | | |
| --- | --- | --- | --- | --- | --- | --- |
|  | Average | Range (%) | | Average | Range (%) | |
| Time (hrs) | (%) | Min | Max | (%) | Min | Max |
| 1 | 2 | 0 | 10 | 1 | 0 | 5 |
| 3 | 12 | 5 | 25 | 5 | 0 | 15 |
| 7 | 33 | 20 | 50 | 25 | 10 | 45 |
| 11 | 56 | 40 | 70 | 51 | 29 | 74 |
| 15 | 73 | 58 | 84 | 68 | 52 | 84 |
| 19 | 81 | 70 | 89 | 79 | 60 | 89 |
| 24 | 85 | 76 | 100 | 93 | 80 | 100 |

The darifenacin and oxybutynin have approximately the same dissolution profile, but the oxybutynin has a slightly faster rate of release and slightly lower total amount released at 24 hours. Although not shown in FIG. 8, the darifenacin can be made to achieve approximately complete dissolution at about 24 hours, and the oxybutynin can be made to achieve approximately complete dissolution at about 20 hours.

In a particular embodiment the controlled release dosage form will provide effective amounts of active agent for a period of not less than 18 hours and not more than 30 hours, or not less than 20 hours and not more than 28 hours, or not less than 22 hours and not more than 24 hours. The artisan of ordinary skill will understand that administration of a single unit dose period of time may be insufficient to maintain therapeutic plasma levels of active agent for up to 24-30 hours and that multiple unit doses administered over an equal number of days may be required to maintain therapeutic plasma levels of active agent for up to 24-30 hours.

Depending upon the particular combination of excipients used, a controlled release dosage form will independently provide an expected overall active agent release profile that is pH-dependent or pH-independent; diffusion or dissolution controlled; pseudo-zero order, zero-order, pseudo-first order, or first-order; or slow, delayed, timed or sustained release or otherwise controlled.

All of the formulations of the invention will provide sufficient levels of each active agent for at least a predetermined period of time to provide a desired therapeutic response.

The external coat can be applied to the surface of a tablet according to methods known to those of ordinary skill in the art. Such methods include, for example, applying solids in solution or suspension through the use of a sprayer that spreads them uniformly over the core or by employing compression or other suitable methods known to those of ordinary skill in the art. The external coat can comprise poly(vinyl pyrrolidone) (PVP) and poly(ethylene glycol) (PEG) and can further comprise materials such as, by way of example and without limitation, hydroxypropyl methylcellulose (HPMC), ethylcellulose (EC), hydroxyethylcellulose (HEC), sodium carboxymethylcellulose (CMC), dimethylaminoethyl methacrylate-methacrylic acid ester copolymer, ethyl acrylate-methyl methacrylate copolymer (GA-MMA), C-5 or 60 SH-50 (Shin-Etsu Chemical Corp.) and combinations thereof. The external coat can also comprise dissolution aids, stability modifiers, and bioabsorption enhancers When the external coat comprises a combination of materials, the relative amounts and ratios of those materials can be varied as desired. For example, when the external coat comprises PVP and PEG, the ratio of PVP:PEG will generally range from about 1-65% by weight of PVP: about 0.1-30% by weight of PEG based upon the weight of the external coat.

When an active agent is present in the external coat, it is present in an amount ranging from about 0.1 to 99% by weight of the coat. This wide range provides great latitude in the design and application of the first tablet. Those of ordinary skill in the art will appreciate that the particular amount of drug employed will vary according to, among other things, the desired pharmacokinetic behavior in a mammal. For example, if the initial burst of drug release is intended to be small, then the external coat might include about 0.01 mg to about 0.5 mg of drug. If the initial burst of drug release is intended to be moderate, the external coat might include about 0.5 mg to about 5 mg of drug. With regard to the level of desired effect provided by an active agent and to the corresponding amount of active agent, the amounts that define small, moderate or large will depend upon the relative inherent activity of the active agent. For example, a potent active agent (one with a high inherent activity) would require substantially lower amounts to provide a small effect than would a moderate active agent (one with moderate inherent activity).

When a rapidly dissolving and/or eroding coat is used in the tablet formulations of the invention, the coat will generally comprise an inert and non-toxic material which is at least partially, and preferably substantially completely, soluble and/or erodible in an environment of use. For example, the rapidly dissolving and/or eroding coat will be soluble and/or erodible in aqueous environments such as, for example, the buccal cavity and/or upper GI tract, e.g., the stomach, duodenum, jejunum or upper small intestines. Exemplary materials are disclosed in U.S. Pat. Nos. 4,576,604 and 4,673,405, and the text *Pharmaceutical Dosage Forms: Tablets Volume I, Second Edition.* (A. Lieberman. ed. 1989, Marcel Dekker, Inc.), the relevant disclosures of which are hereby incorporated by reference. In preferred embodiments, the rapidly dissolving and/or erodible coat will be soluble and/or erodible in saliva, gastric juices, or acidic fluids.

The long acting controlled release tablet formulations that provide a delayed and sustained release of active agent may include an enteric coat which is soluble or erodible in intestinal juices, substantially pH neutral or basic fluids but for the most part insoluble in gastric juices or acidic fluids. A wide variety of other polymeric materials are known to possess these various solubility properties. Such other polymeric materials include, by way of example and without limitation, cellulose acetate phthalate (CAP), cellulose acetate trimelletate (CAT), poly(vinyl acetate) phthalate (PVAP), hydroxypropyl methylcellulose phthalate (HP), poly(methacrylate ethyl acrylate) (1:1) copolymer (MA-EA), poly(methacrylate methyl methacrylate) (1:1) copolymer (MA-MMA), poly (methacrylate methyl methacrylate) (1:2) copolymer, Eudragit L-30-D™ (MA-EA, 1:1), Eudragit™ L-100-55™ (MA-EA, 1:1), hydroxypropyl methylcellulose acetate succinate (HPMCAS), Coateric™ (PVAP), Aquateric™ (CAP), AQUACOAT™ (HPMCAS) and combinations thereof. The enteric coat can also comprise dissolution aids, stability modifiers, and bioabsorption enhancers.

When the enteric coat is intended to be dissolved, eroded or become detached from the core in the colon materials such as hydroxypropylcellulose, microcrystalline cellulose (MCC, Avicel™ from FMC Corp.), poly(ethylene-vinyl acetate) (60:40) copolymer (EVAC from Aldrich Chemical Co.), 2-hydroxyethylmethacrylate (HEMA), MMA, terpolymers of HEMA: MMA:MA synthesized in the presence of N,N'-bis (methacryloyloxyethyloxycarbonylamino)-azobenzene, azopolymers, enteric coated timed release system (Time Clock® from Pharmaceutical Profiles, Ltd., UK) and calcium pectinate can be used.

A polymeric material for use in the enteric coat involves materials that resist the action of gastric fluid avoiding permeation through the semipermeable wall while one or more of the materials in the core of the tablet are solubilized in the intestinal tract thereby allowing delivery of the drug in the core by osmotic pumping in an osmotic device to begin. A material that easily adapts to this kind of requirement is a poly(vinylpyrrolidone)-vinyl acetate copolymer, such as the material supplied by BASF under its Kollidon VA64 trademark, mixed with magnesium stearate and other similar excipients. The enteric coat can also comprise povidone, which is supplied by BASF under its Kollidon K 30 trademark, and hydroxypropyl methylcellulose, which is supplied by Dow under its Methocel E-15 trademark. The materials can be prepared in solutions of having different concentrations of polymer according to the desired solution viscosity. For example, a 10% P/V aqueous solution of Kollidon K 30 has a viscosity of about 5.5-8.5 cps at 20° C., and a 2% P/V aqueous solution of Methocel E-15 has a viscosity of about 13-18 cps at 20° C.

The enteric coat can comprise one or more materials that do not dissolve, disintegrate, or change their structural integrity in the stomach and during the period of time that the tablet resides in the stomach. Representative materials that keep their integrity in the stomach can comprise a member selected from the group consisting of (a) keratin, keratin sandarac-tolu, salol (phenyl salicylate), salol beta-naphthylbenzoate and acetotannin, salol with balsam of Peru, salol with tolu, salol with gum mastic, salol and stearic acid, and salol and shellac; (b) a member selected from the group consisting of formalized protein, formalized gelatin, and formalized crosslinked gelatin and exchange resins; (c) a member selected from the group consisting of myristic acid-hydrogenated castor oil-cholesterol, stearic acid-mutton tallow, stearic acid-balsam of tolu, and stearic acid-castor oil; (d) a member selected from the group consisting of shellac, ammoniated shellac, ammoniated shellac-salol, shellac-wool fat, shellac-acetyl alcohol, shellac-stearic acid-balsam of tolu, and shellac n-butyl stearate; (e) a member selected from the group consisting of abietic acid, methyl abictate, benzoin, balsam of tolu, sandarac, mastic with tolu, and mastic with tolu, and mastic with acetyl alcohol; (f) acrylic resins represented by anionic polymers synthesized from methacrylate acid and methacrylic acid methyl ester, copolymeric acrylic resins of methacrylic and methacrylic acid and methacrylic acid alkyl esters, copolymers of alkacrylic acid and alkacrylic acid alkyl esters, acrylic resins such as dimethylaminoethylmethacrylate-butylmethacrylate-methylmethacrylate copolymer of 150,000 molecular weight, methacrylic acid-methyl methacrylate 50:50 coplomer of 135,000 molecular weight, methacrylic acid-methylmethacrylate-30:70-copolymer of 135,000 mol. wt., methacrylic acid-dimethylaminoethyl-methacrylate-ethyl acrylate of 750,000 mol. wt., methacrylic acid-methyl methacrylate-ethyl acrylate of 1,000,000 mol. wt., and ethyl acrylate-methyl methacrylate-ethyl acrylate of 550,000 mol. wt; and, (g) an enteric composition comprising a member selected from the group consisting of cellulose acetyl phthalate, cellulose diacetyl phthalate, cellulose triacetyl phthalate, cellulose acetate phthalate, hydroxypropyl methylcellulose phthalate, sodium cellulose acetate phthalate, cellulose ester phthalate, cellulose ether phthalate, methylcellulose phthalate, cellulose ester-ether phthalate, hydroxypropyl cellulose phthalate, alkali salts of cellulose acetate phthalate, alkaline earth salts of cellulose acetate phthalate, calcium salt of cellulose acetate phthalate, ammonium salt of hydroxypropyl methylcellulose phthalate, cellulose acetate hexahydrophthalate, hydroxypropyl methylcellulose hexahydrophthalate, polyvinyl acetate phthalate diethyl phthalate, dibutyl phthalate, dialkyl phthalate wherein the alkyl comprises from 1 to 7 straight and branched alkyl groups, aryl phthalates, and other materials known to one or ordinary skill in the art.

The wall of the osmotic device can be semipermeable or microporous. When the wall is a semipermeable membrane, the semipermeable membrane can be formed of a material that is substantially permeable to the passage of fluid from the environment of use to the core and substantially impermeable to the passage of active agent from the core. Many common materials known by those of ordinary skill in the art are suitable for this purpose. Exemplary materials are cellulose esters, cellulose diesters, cellulose triesters, cellulose ethers, cellulose ester-ether, cellulose acylate, cellulose diacylate, cellulose triacylate, cellulose acetate, cellulose diacetate, cellulose triacetate, cellulose acetate propionate, cellulose acetate butyrate and ethylcellulose and combinations thereof. Preferred semipermeable membrane materials are cellulose acetates comprising an acetyl content of 39.3 to 40.3% and 31.0 to 33.0%, commercially available under the tradename CA 398-10, CA 398-3 and CA320S from Eastman Fine Chemicals. The semipermeable membrane composition can comprise a flux enhancing agent. The flux enhancing agent increase the volume of fluid imbibed into the core to enable the dosage form to release substantially all of the active agents through both the passageway and the porous membrane. The flux enhancing agent is a water-soluble component such as sodium chloride, potassium chloride, sucrose, sorbitol, mannitol, sugar, polyethylene glycol (molecular weight 380-3700), propylene glycol, hydroxypropyl cellulose, hydroxypropyl methylcellulose and mixtures thereof. The preferred flux enhancer is PEG 400. The semipermeable membrane can also comprise commonly known excipients such a plasticizer. Exemplary plasticizers are enzoate, citrate, stearate, azelate, isoebucate, sebacate, triethyl citrate, tri-n- butyl citrate, adipate, acetyl tri-n-butyl citrate, citric acid esters, and those described in the *Handbook of Pharmaceutical Excipients*, 3$^{rd}$ ed. (2000), published by the American Pharmaceutical Association, the entire disclosures of which is hereby incorporated by reference. The preferred plasticizer is triacetin but materials such as acetylated monoglyceride, acetyltributylcitrate, acetyltriethylcitrate, sesame oil, rape seed oil, olive oil, glycerin sorbitol, diethyloxalate, diethylmalate, diethylmalonate, diethylfumarate, dibutylsuccinate, dioctylphthalate, dibutylsebacate, triethylcitrate, tributylcitrate, glyceroltributyrate, and the like can also be used. When the wall is microporous, the micropores can be formed during preparation of the wall, or during exposure to fluids in an intended environment of use. Methods of preparing walls wherein the micropores form in the environment of use are well known and described in, among others, U.S. Pat. No. 3,845,770, U.S. Pat. No. 3,916,899, U.S. Pat. No. 4,063,064, U.S. Pat. No. 4,088,864, U.S. Pat. No. 4,816,263, U.S. Pat. No. 4,200,098, U.S. Pat. No. 4,285,987 and No. 5,912,268, the relevant disclosures of which are hereby incorporated by reference.

Osmotically effective compounds, such as osmotic agents or osmagents and osmopolymers, suitable for manufacturing the composition of the layers of the core, can create an osmotic pressure gradient across the wall when the osmotic device is in an aqueous environment; accordingly, the fluid and components of the layers of the core will generally form a solution or suspension comprising the active agent to be delivered. Swellable hydrophilic polymers suitable for manufacturing the composition of the layers of the core can include hydrophilic polymers that interact with water and/or aqueous biological fluids, and swell and retain water within their structure. The polymers are preferably slightly cross-linked. Uncross-linked polymers will preferably not dissolve in water, keeping their physical integrity. The polymers are of animal, plant or synthetic origin. Hydrophilic polymers suitable for manufacturing the core of the invention preferably include hydroxypropyl methylcelluloses (viscosity from 3 to 100,000 cps, measured in 2% w/v solution); ethylcelluloses (viscosity from 3 to 110 cP, measured in 5% w/v solution); methylcelluloses (viscosity from 10 to 10,000 cP, measured in 2% w/v solution); hydroxypropylcelluloses (general average molecular weight of about 80,000 to 1,150,000); hydroxyethylcelluloses (viscosity from 2 to 21,000 cP, measured in 2% w/v solution); carboxymethylcelluloses (viscosity from 5 to 4,000 cP, measured in 1% w/v solution); poly(alkylene) oxide that might include homopolymer of ethylene oxide, propylene oxide and butylene oxide and copolymers of those. Osmagents suitable for manufacturing the composition of the layers of the core can include high or low molecular weight compounds, organic and inorganic compounds such as salts, acids, bases, chelating agents, sodium chloride, lithium chloride, magnesium chloride, magnesium sulfate, lithium sulfate, potassium chloride, sodium sulfite, calcium bicarbonate, sodium sulfate, calcium sulfate, calcium lactate, d-mannitol, urea, tartaric acid, raffinose, sucrose, alpha-d-lactose monohydrate, glucose, combinations thereof and other similar or equivalent materials known to those of ordinary skill in the art. Preferred osmagents include potassium chloride, sodium tartrate, glucose, mannitol, sodium acetate, sodium chloride, sodium sulfate, sodium citrate, potassium tartrate, sorbitol, sucrose and combinations thereof.

The osmotic device of the invention comprises at least one preformed passageway (pore, hole, or aperture) that communicates the exterior of the semipermeable wall with the core of the device. The preformed passageway can be formed according to any of the known methods of forming passageways in a membrane. Such methods include, for example, 1) drilling a hole through the semipermeable membrane with a bit or laser; 2) including a water soluble material within the composition that forms the semipermeable membrane such that a pore forms when the osmotic device is in an aqueous environment of use; 3) punching a hole through the semipermeable membrane; or 4) employing a tablet punch having a pin to punch a hole through the semipermeable lamina. The preformed passageway can pass through the semipermeable wall and one or more of any other lamina coated onto the semipermeable membrane or between the semipermeable membrane and the core. The passageway(s) can be shaped as desired. In some embodiments, the passageway is laser drilled and is shaped as an oval, ellipse, slot, slit, cross or circle. Micropores in a microporous membrane are distinguished from preformed passageways.

The depth of penetration of a preformed passageway can be tailored to provide specific active agent release profiles, to control the extent to which release of an active agent is delayed, and/or to control the order in which active agents are released. The order in which the process steps of forming a preformed passageway and applying a coating composition are conducted can be performed to provide specific active agent release profiles, to control the extent to which release of a active agent is delayed, and/or to control the order in which drugs are released.

Methods of forming passageways in the wall of the present dosage form are disclosed in U.S. Pat. No. 4,088,864 to Theeuwes et al., U.S. Pat. No. 4,016,880 to Theeuwes et al., U.S. Pat. No. 3,916,899 to Theeuwes et al., U.S. Pat. No. 4,285,987 to Ayer et al., U.S. Pat. No. 4,783,337 to Wong et al., U.S. Pat. No. 5,558,879 to Chen et al., U.S. Pat. No. 4,801,461 to Hamel et al., and U.S. Pat. No. 3,845,770 to Theeuwes et al., the disclosures of which are hereby incorporated by reference.

When the controlled release tablet is an osmotic device, osmotically effective solutes, osmotic agents or osmagents are added. These osmagents will aid in either the suspension or dissolution of oxybutynin and the second drug in the core. Exemplary osmagents include organic and inorganic compounds such as salts, acids, bases, chelating agents, sodium chloride, lithium chloride, magnesium chloride, magnesium sulfate, lithium sulfate, potassium chloride, sodium sulfite, calcium bicarbonate, sodium sulfate, calcium sulfate, calcium lactate, d-mannitol, urea, tartaric acid, raffinose, sucrose, alpha-d-lactose monohydrate, glucose, combinations thereof and other similar or equivalent materials which are widely known in the art.

The tablets of the invention can also comprise adsorbents, antioxidants, buffering agents, colorants, flavorants, sweetening agents, tablet antiadherents, tablet binders, tablet and capsule diluents, tablet direct compression excipients, tablet disintegrants, tablet glidants, tablet lubricants, tablet or capsule opaquants and/or tablet polishing agents.

As used herein, the term "adsorbent" is intended to mean an agent capable of holding other molecules onto its surface by physical or chemical (chemisorption) means. Such compounds include, by way of example and without limitation, powdered and activated charcoal and other materials known to one of ordinary skill in the art.

As used herein, the term "antioxidant" is intended to mean an agent which inhibits oxidation and thus is used to prevent the deterioration of preparations by the oxidative process. Such compounds include, by way of example and without limitation, ascorbic acid, ascorbyl palmitate, butylated hydroxyanisole, butylated hydroxytoluene, hypophosphorous acid, monothioglycerol, propyl gallate, sodium ascorbate, sodium bisulfite, sodium formaldehyde sulfoxylate and sodium metabisulfite and other materials known to one of ordinary skill in the art.

As used herein, the term "buffering agent" is intended to mean a compound used to resist change in pH upon dilution or addition of acid or alkali. Such compounds include, by way of example and without limitation, potassium metaphosphate, potassium phosphate, monobasic sodium acetate and sodium citrate anhydrous and dehydrate and other materials known to one of ordinary skill in the art.

As used herein, the term "sweetening agent" is intended to mean a compound used to impart sweetness to a preparation. Such compounds include, by way of example and without limitation, aspartame, dextrose, glycerin, mannitol, saccharin sodium, sorbitol and sucrose and other materials known to one of ordinary skill in the art.

As used herein, the term "tablet antiadherents" is intended to mean agents which prevent the sticking of tablet formulation ingredients to punches and dies in a tableting machine during production. Such compounds include, by way of example and without limitation, magnesium stearate, talc, calcium stearate, glyceryl behenate, PEG, hydrogenated vegetable oil, mineral oil, stearic acid and other materials known to one of ordinary skill in the art.

As used herein, the term "tablet binders" is intended to mean substances used to cause adhesion of powder particles in table granulations. Such compounds include, by way of example and without limitation, acacia, alginic acid, carboxymethylcellulose sodium, poly(vinylpyrrolidone), compressible sugar (e.g., NuTab), ethylcellulose, gelatin, liquid glucose, methylcellulose, povidone and pregelatinized starch and other materials known to one of ordinary skill in the art.

When needed, binders may also be included in the tablets. Exemplary binders include acacia, tragacanth, gelatin, starch, cellulose materials such as methyl cellulose and sodium carboxy methyl cellulose, alginic acids and salts thereof, polyethylene glycol, guar gum, polysaccharide, bentonites, sugars, invert sugars, poloxamers (PLURONIC F68, PLURONIC F127), collagen, albumin, gelatin, cellulosics in nonaqueous solvents, combinations thereof and the like. Other binders include, for example, polypropylene glycol, polyoxyethylene-polypropylene copolymer, polyethylene ester, polyethylene sorbitan ester, polyethylene oxide, combinations thereof and other materials known to one of ordinary skill in the art.

As used herein, the term "tablet and capsule diluent" or "fillers" is intended to mean inert substances used as fillers to create the desired bulk, flow properties, and compression characteristics in the preparation of tablets and capsules. Such compounds include, by way of example and without limitation, dibasic calcium phosphate, kaolin, lactose, sucrose, mannitol, microcrystalline cellulose, powdered cellulose, precipitated calcium carbonate, sorbitol, and starch and other materials known to one of ordinary skill in the art.

As used herein, the term "tablet direct compression excipient" is intended to mean a compound used in direct compression tablet formulations. Such compounds include, by way of example and without limitation, dibasic calcium phosphate (e.g., Ditab) and other materials known to one of ordinary skill in the art.

As used herein, the term "tablet glidant" is intended to mean agents used in tablet and capsule formulations to promote flowability of the granulation. Such compounds include, by way of example and without limitation, colloidal silica, cornstarch, talc, calcium silicate, magnesium silicate, colloidal silicon, silicon hydrogel and other materials known to one of ordinary skill in the art.

As used herein, the term "tablet lubricant" is intended to mean substances used in tablet formulations to reduce friction during tablet compression. Such compounds include, by way of example and without limitation, calcium stearate, magnesium stearate, mineral oil, stearic acid, and zinc stearate and other materials known to one of ordinary skill in the art.

As used herein, the term "tablet/capsule opaquant" is intended to mean a compound used to render a capsule or a tablet coating opaque. May be used alone or in combination with a colorant. Such compounds include, by way of example and without limitation, titanium dioxide and other materials known to one of ordinary skill in the art.

As used herein, the term "tablet polishing agent" is intended to mean a compound used to impart an attractive sheen to coated tablets. Such compounds include, by way of example and without limitation, carnauba wax, and white wax and other materials known to one of ordinary skill in the art.

As used herein, the term "tablet disintegrant" is intended to mean a compound used in solid dosage forms to promote the disruption of the solid mass into smaller particles which are more readily dispersed or dissolved. Exemplary disintegrants include, by way of example and without limitation, starches such as corn starch, potato starch, pre-gelatinized and modified starches thereof, sweeteners, clays, such as bentonite, microcrystalline cellulose (e.g., Avicel), carboxymethylcellulose calcium, cellulose polyacrilin potassium (e.g., Amberlite), alginates, sodium starch glycolate, gums such as agar, guar, locust bean, karaya, pectin, tragacanth and other materials known to one of ordinary skill in the art.

As used herein, the term "colorant" is intended to mean a compound used to impart color to solid (e.g., tablets) pharmaceutical preparations. Such compounds include, by way of example and without limitation, FD&C Red No. 3, FD&C Red No. 20, FD&C Yellow No. 6, FD&C Blue No. 2, D&C Green No. 5, D&C Orange No. 5, D&C Red No. 8, caramel, and ferric oxide, red, other F.D. & C. dyes and natural coloring agents such as grape skin extract, beet red powder, beta-carotene, annato, carminic acid, turmeric, paprika, and other materials known to one of ordinary skill in the art. The amount of coloring agent used will vary as desired.

As used herein, the term "flavorant" is intended to mean a compound used to impart a pleasant flavor and often odor to a pharmaceutical preparation. Exemplary flavoring agents or flavorants include synthetic flavor oils and flavoring aromatics and/or natural oils, extracts from plants, leaves, flowers, fruits and so forth and combinations thereof. These may also include cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Other useful flavors include vanilla, citrus oil, including lemon, orange, grape, lime and grapefruit, and fruit essences, including apple, pear, peach, strawberry, raspberry, cherry, plum, pineapple, apricot and so forth. Flavors that have been found to be particularly useful include commercially available orange, grape, cherry and bubble gum flavors and mixtures thereof. The amount of flavoring may depend on a number of factors, including the organoleptic effect desired. Flavors will be present in any amount as desired by those of ordinary skill in the art. Particularly preferred flavors are the grape and cherry flavors and citrus flavors such as orange.

The present formulations can also employ one or more commonly known surface active agents or cosolvents that improve wetting or disintegration of the tablet core or layers.

Plasticizers can also be included in the formulations to modify the properties and characteristics of the polymers used in the coats or core of the tablets. As used herein, the term "plasticizer" includes all compounds capable of plasticizing or softening a polymer or binder used in invention. The plasticizer should be able to lower the melting temperature or glass transition temperature (softening point temperature) of the polymer or binder. Plasticizers, such as low molecular weight PEG, generally broaden the average molecular weight of a polymer in which they are included thereby lowering its glass transition temperature or softening point. Plasticizers also generally reduce the viscosity of a polymer. It is possible the plasticizer will impart some particularly advantageous physical properties to the osmotic device of the invention.

Plasticizers useful in the invention can include, by way of example and without limitation, low molecular weight polymers, oligomers, copolymers, oils, small organic molecules, low molecular weight polyols having aliphatic hydroxyls, ester-type plasticizers, glycol ethers, poly(propylene glycol), multi-block polymers, single block polymers, low molecular weight poly(ethylene glycol), citrate ester-type plasticizers, triacetin, propylene glycol and glycerin. Such plasticizers can also include ethylene glycol, 1,2-butylene glycol, 2,3-butylene glycol, styrene glycol, diethylene glycol, triethylene glycol, tetraethylene glycol and other poly(ethylene glycol) compounds, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutylsebacate, acetyltributylcitrate, triethyl citrate, acetyl triethyl citrate, tributyl citrate and allyl glycolate. All such plasticizers are commercially available from sources such as Aldrich or Sigma Chemical Co. It is also contemplated and within the scope of the invention, that a combination of plasticizers may be used in the present formulation. The PEG based plasticizers are available commercially or can be made by a variety of methods, such as disclosed in *Poly(ethylene glycol) Chemistry: Biotechnical and Biomedical Applications* (J. M. Harris, Ed.; Plenum Press, NY) the disclosure of which is hereby incorporated by reference.

The formulations of the invention can also include oils, for example, fixed oils, such as peanut oil, sesame oil, cottonseed oil, corn oil and olive oil; fatty acids, such as oleic acid, stearic acid and isotearic acid; and fatty acid esters, such as ethyl oleate, isopropyl myristate, fatty acid glycerides and acetylated fatty acid glycerides. It can also be mixed with alcohols, such as ethanol, isopropanol, hexadecyl alcohol, glycerol and propylene glycol; with glycerol ketals, such as 2,2-dimethyl-1,3-dioxolane-4-methanol; with ethers, such as poly(ethyleneglycol) 450, with petroleum hydrocarbons, such as mineral oil and petrolatum; with water, or with mixtures thereof; with or without the addition of a pharmaceutically suitable surfactant, suspending agent or emulsifying agent.

Soaps and synthetic detergents may be employed as surfactants and as vehicles for detergent compositions. Suitable soaps include fatty acid alkali metal, ammonium, and triethanolamine salts. Suitable detergents include cationic detergents, for example, dimethyl dialkyl ammonium halides, alkyl pyridinium halides, and alkylamine acetates; anionic detergents, for example, alkyl, aryl and olefin sulfonates, alkyl, olefin, ether and monoglyceride sulfates, and sulfosuccinates; nonionic detergents, for example, fatty amine oxides, fatty acid alkanolamides, and poly(oxyethylene)-block-poly (oxypropylene) copolymers; and amphoteric detergents, for example, alkyl β-aminopropionates and 2-alkylimidazoline quaternary ammonium salts; and mixtures thereof.

Various other components, not otherwise listed above, can be added to the present formulation for optimization of a desired active agent release profile including, by way of example and without limitation, glycerylmonostearate, nylon, cellulose acetate butyrate, d, 1-poly(lactic acid), 1,6-hexanediamine, diethylenetriamine, starches, derivatized starches, acetylated monoglycerides, gelatin coacervates, poly(styrene-maleic acid) copolymer, glycowax, castor wax, stearyl alcohol, glycerol palmitostearate, poly(ethylene), poly(vinyl acetate), poly(vinyl chloride), 1,3-butylene-glycoldimethacrylate, ethyleneglycol-dimethacrylate and methacrylate hydrogels.

It should be understood, that compounds used in the art of pharmaceutical formulation generally serve a variety of functions or purposes. Thus, if a compound named herein is mentioned only once or is used to define more than one term herein, its purpose or function should not be construed as being limited solely to that named purpose(s) or function(s).

The term "unit dose" is used herein to mean an amount of the pharmaceutical composition that is included in one or more dosage forms that together provide a therapeutically effective amount of an active agent. Depending upon the specific combination and amounts of active agent included within the dosage form, an improved, additive or synergistic therapeutic effect will be observed. Accordingly, a unit dose may include therapeutic or sub-therapeutic amounts of each active agent. An improved therapeutic effect is one wherein the one active agent enhances the therapeutic benefit provided by another active agent alone. An additive therapeutic effect is one wherein each of two different active agents possesses therapeutic properties, and the combination of the two active agents provides an overall therapeutic effect that approximates the sum of their individual therapeutic effects. A synergistic therapeutic effect is one wherein each of two different active agents possesses therapeutic properties, and the combination of the two active agents provides an overall therapeutic effect that is greater than the sum of their individual therapeutic effects. In each embodiment of the invention, a particular combination of drugs will provide at least an improved clinical benefit as compared to the individual drugs.

As used herein, the term clinical benefit refers to an improvement in therapeutic efficacy, safety, pharmacokinetics, pharmacodynamics, and/or symptomatology.

By the term "effective amount", it is understood that, with respect to, for example, pharmaceuticals, a therapeutically or sub-therapeutically effective amount is contemplated. A therapeutically effective amount is the amount or quantity of active agent that is sufficient to elicit the required or desired therapeutic response, or in other words, the amount that is sufficient to elicit an appreciable biological response when administered to a patient. A sub-therapeutically effective amount is an amount that is less than the therapeutically effective amount when the dosage form of the invention is administered to a subject. The pharmaceutical composition and dosage form of the invention can contain therapeutically effective or sub-therapeutically effective amounts of each active agent.

Tablets can differ in size, shape, color and amount of active agent. The tablets of the invention can assume any shape or form known in the art of pharmaceutical sciences. The device of the invention can be a pill, sphere, tablet, bar, plate, paraboloid of revolution, ellipsoid of revolution or other shape known to those of ordinary skill in the art. The tablets can also include surface markings, cuttings, grooves, letters and/or numerals for the purposes of decoration, identification and/or other purposes.

The tablets of the invention can be prepared according to the methods disclosed herein or those well known in the art, more also according to the methods disclosed in the disclosures incorporated herein by reference. For example, according to one manufacturing technique, each active agent is included in its own respective composition. A charge of the first or second composition is then compressed with a tablet punch to form the first portion of the core. A charge of the second or first composition, respectively, is then loaded onto the compressed first charge and compressed as well to form the bilayered core. The uncoated cores are then dried in a dryer and compressed, for example, by punching. The compressed and uncoated cores are then covered with a solution of suitable materials to provide the desired drug release profile. For example, if the tablet is to be an osmotic device, then the tablet core may be coated with a semipermeable membrane. Subsequently, the semipermeable membrane surrounding the core should be perforated with, for example, laser equipment.

The tablets of the invention can be coated with a finish coat as is commonly done in the art to provide the desired shine, color, taste or other aesthetic characteristics. Materials suitable for preparing the finish coat are well known in the art and found in the disclosures of many of the references cited and incorporated by reference herein. A finish coat is generally water soluble or water erodible. The finish coat will plug a preformed passageway that has been formed just prior to application of the finish coat.

The pharmaceutical compositions employed in the dosage form can be a homogeneous or heterogeneous mixture of the components therein. The dosage form comprises at least two different compositions, such as a first composition comprising a first active agent and a second composition comprising a second active agent. The first and second compositions can be stacked in the core of a solid dosage form or one of the first and second compositions can surround the other composition.

Active agents useful in the delivery device include, for example, compounds such as biologically or pharmacologically active agents, medicines, nutrients, food products, insecticides, pesticides, herbicides, germicides, algaecides, fungicides, chemical reagents, growth regulating substances, parasiticides, sex sterilants, fertility promoters, biocides, rodenticides, disinfectants, anti-oxidants, plant growth promoters, preservatives, fermentation agents, fertility inhibitors, deodorants, micro-organism attenuators, catalysts, food supplements, cosmetics, vitamins, and other agents that benefit the environment of use.

The dosage form of the invention may be used in biological environments, aquariums, industrial warehouses, laboratory facilities, hospitals, chemical reactions and other facilities.

Various different types of active agents can be included in the dosage form of the invention. The active agent is independently selected at each occurrence from the group consisting of an antibiotic agent, antihistamine agent, decongestant, anti-inflammatory agent, antiparasitic agent, antiviral agent, local anesthetic, antifungal agent, amoebicidal agent, trichomonocidal agent, analgesic agent, anti-arthritic agent, anti-asthmatic agent, anticoagulant agent, anticonvulsant agent, antidepressant agent, antidiabetic agent, antineoplastic agent, anti-psychotic agent, neuroleptic agent, antihypertensive agent, hypnotic agent, sedative agent, anxiolytic energizer agent, anti-Parkinson agent, muscle relaxant agent, antimalarial agent, hormonal agent, contraceptive agent, sympathomimetic agent, hypoglycemic agent, antilipemic agent, ophthalmic agent, electrolytic agent, diagnostic agent, prokinetic agent, gastric acid secretion inhibitor agent, antiulcerant agent, anti-flatulent agent, anti-incontinence agent, and cardiovascular agent. The invention is particularly useful for the combined administration of drugs of different types. Exemplary combinations that are suitable for administration include, for example, those wherein: 1) the first active agent is a prokinetic agent and the second active agent is a gastric acid secretion inhibitor agent; 2) the first active agent is a decongestant and the second active agent is an antihistamine; 3) the first active agent is a first anti-incontinence agent and the second active agent is a different second anti-incontinence agent; 4) the first active agent is a first antihypertensive agent and the second active agent is a different second antihypertensive agent; 5) the first active agent is an antidepressant agent and the second active agent is an anti-psychotic agent; 6) the first active agent is a first analgesic or anti-inflammatory agent, and the second active agent is a different second analgesic or anti-inflammatory agent; 7) the first active agent is an antiviral agent and the second active agent is an antihistamine agent; 8) the first active agent is a muscle relaxant agent and the second active agent is an anti-inflammatory or analgesic agent; 9) the first active agent is an antidiabetic agent and the second active agent is a different antidiabetic agent; 10) the first active agent is an antidepressant and the second active agent is an agent for the treatment of Alzheimer's disease; 11) the first active agent is an anticonvulsant and the second active agent is an anti-psychotic agent; 12) the first active agent is an antilipemic agent and the second active agent is a different antilipemic agent; 13) the first active agent is an antidepressant and the second active agent is an anti-Parkinson agent; and 14) the first active agent is an antidiabetic agent and the second active agent is an antilipemic agent.

Specific embodiments include those wherein: 1) the first active agent is pridinol and the second active agent is a selective or specific COX-II inhibitor agent; 2) the analgesic and anti-inflammatory agents are selected from the group consisting of an non-steroidal anti-inflammatory agent, a steroidal, anti-inflammatory agent, an opioid receptor agonist agent, and a selective or specific COX-II inhibitor agent; 3) the antihypertensive agents are selected from the group consisting of a calcium channel blocker agent, an angiotensin converting enzyme inhibitor agent, a diuretic agent and a beta-adrenergic antagonist agent; 4) the diabetic agents are selected from the following main groups of oral antidiabetic drugs available: sulphonylureas, such as tolbutamide, chlorpropamide, tolazamide, acetohexamide, glibenclamide, gliclazide, 1-butyl-3-metanilylurea, carbutamide, glibonuride, glipizide, glyburide, gliquidone, glisoxepid, glybuthiazole, glibuzole, glyhexamide, glymidine, glypinamide, phenbutamide, and tolcyclamide; thiazolidinediones (glitazones), such as rosiglitazone, pioglitazone, and troglitazone; biguanidines, such as metformin; and other antidiabetic agents, such as nateglinide and repaglinide; 5) the agent for the treatment of Alzheimer's disease is selected from the group consisting of memantine, donepezil, galantamine, rivastigmine, and tacrine; 6) the antidepressant is selected from the group consisting of venlafaxine, amitriptyline, citalopram, bupropion, clomipramine, desipramine, nefazodone, fluoxetine, doxepin, fluvoxamine, maprotiline, imipramine, mirtazapine, nortriptyline, paroxetine, phenelzine, tranylcypromine, protriptyline, sertraline, trazodone, trimipramine, and amoxapine; 7) the anticonvulsant is selected from the group consisting of carbamazepine, lamotrigine, levetiracetam, oxcarbazepine, topiramate, and zonisamide; 8) the antipsychotic agent is selected from the group consisting of chlorpromazine, clozapine, fluphenazine, haloperidol, loxapine, mesoridazine, molindone, olanzapine, quetiapine, ziprasidone, risperidone, perphenazine, pimozide, prochlorperazine, thioridazine, thiothixene, and trifluoperazine; 9) the antilipemic agent is selected from the group consisting of cholestyramine, cholestipol, nicotinic acid, clofibrate, gemfibrozil, dextrothyroxine sodium, prabucol, mevastatin, lovastatin, simvastatin, pravastatin, fluvastatin, atorvastatin, pitavastatin, and ezetimibe; 10) the anti-Parkinson agent is selected from the group consisting of levodopa, benztropine mesylate, benzeraside, carbidopa, bromocriptine, pergolide, selegiline, ropirinol, pramipexole, amantadine, entacapone, tolcapone, biperiden, carbelogine, apomorphine, lisuride, prociclidine, and trihexyphenidyl; and 11) the first active agent is pridinol and the second active agent is licofelone.

As used herein, the terms "very soluble", "freely soluble", "soluble", "sparingly soluble", "slightly soluble", "very slightly soluble", and "practically insoluble" or "insoluble" are defined as they are defined in the U.S.P. 23$^{rd}$ Ed. as follows:

| Term | Solubility of component in water (parts of solvent per part of component) |
| --- | --- |
| Very soluble | <1 |
| Freely soluble | 1-10 |
| Soluble | 10-30 |
| Sparingly soluble | 30-100 |
| Slightly soluble | 100-1,000 |
| Very slightly soluble | 1,000-10,000 |
| Practically insoluble or insoluble | Over 10,000 |

The present delivery device can be adapted to permit delivery of a first and a second active agent having very similar to very different water solubility. For example, by varying the particular combination of excipients used in the composition of the layers, and/or the thickness and/or the surface area of the semipermeable membrane, and/or the geometry (shape) of the first and second compositions, and/or the number and/or size and/or distribution of the passageways. Representative very soluble active agents useful for the invention are amoxicilin sodium, clorpromazine, hydroxyzine, levetiracetam, meperidine HCl, metoprolol tartrate, rabeprazole sodium, ranitidine HCl, rivastigmine hydrogen tartrate, venlafaxine HCl, and warfarin sodium, among others known to those of ordinary skill in the art.

Representative freely soluble active agents useful for the invention are amitriptyline, buspirone HCl, captopril, cephazolin sodium, cyclobenzaprine HCl, diltiazem HCl, gabapentin, isosorbide mononitrate, losartan potassium, metformin HCl, montelukast sodium, propoxiphene HCl, pseudoephedrine HCl, quinapril, and tramadol HCl, among others known to those of ordinary skill in the art.

Representative soluble active agents useful for the invention are alendronate sodium, benazepril, bupropion HCl, cetirizine, clonidine HCl, doxycycline hydrate, fosinopril sodium, hydrocodone bitartrate, levofloxacin, lisinopril, meclizine HCl, oxybutynin HCl, oxycodone, phenyloin sodium, pravastatin sodium, verapamil HCl, rosiglitazone maleate, promethazine HCl, propranolol HCl, and sumatriptan, among others known to those of ordinary skill in the art.

Representative sparingly soluble active agents useful for the invention are albuterol, atenolol, caffeine monohydrate, cimetidine, ciprofloxacin HCl monohydrate, citalopram, enalapril maleate, fluoxetine HCl, galantamine HBr, metronidazole, salmeterol, trazodone HCl, and zolpiden tartrate, among others known to those of ordinary skill in the art.

Representative slightly soluble active agents useful for the invention are acyclovir, amlodipine besylate, amoxicilin trihydrate, aspirin, carisoprodol, doxazosin mesylate, fexofenadine HCl, fluconazole, memantine HCl, paroxetine HCl, ramipril, sertraline HCl, sildenafil citrate, and valsartan, among others known to those of ordinary skill in the art.

Representative very slightly soluble active agents useful for the invention are acetaminophen, allopurinol, atorvastatin calcium, genfibrozil, ibuprofen, omeprazole, prednisone, ralozifene HCL and temazepan, among others known to those of ordinary skill in the art.

Representative practically insoluble active agents useful for the invention are alprazolam, azithromycin dihydrate, carbamazepine, carvedilol, celecoxib, cisapride monohydrate, clonazepam, clopidogrel bisulfate, ciprofloxacin HCl, diazepam, felodipine, fluticasone propionate, glipizide, glyburide, hydrochlorothiazide, lansoprazole, loratadine, lorazepam, mometasone furoate, naproxen, nifedipine, nisoldipine, olanzapine, pindolol, pioglitazone HCl, risperidone, rofecoxib, simvastatin and triamtirene, among others known to those of ordinary skill in the art.

The invention provides a method of treating a disease, condition, illness or symptom in a subject comprising the step of administering to the subject, suffering from the disease, condition, illness or symptom, at least one dosage form according to the invention whereby an effective amount of at two different active agents is provided to the subject. The period of treatment as well as the number of treatments needed to treat the disease, condition, illness or symptom may vary according to a subject's health, physical condition, diet, gender, competing pathologies and/or age as well as the severity of the disease, condition, illness or symptom.

The invention also provides a method of preventing a disease, condition, illness or symptom in a subject comprising the step of administering to a subject predisposed to the disease, condition, illness or symptom at least one dosage form according to the invention prior to the occurrence of the disease, condition, illness or symptom in the subject, whereby an effective amount of at two different active agents is provided to the subject and the disease, condition, illness or symptom is prevented. The period of treatment as well as the number of treatments needed to prevent the disease, condition, illness or symptom may vary according to a subject's health, physical condition, diet, gender, competing pathologies and/or age as well as the extent to which the subject is predisposed to suffer from the disease, condition, illness or symptom.

The method of the invention can comprise the steps of determining the pharmacokinetic, pharmacodynamic, pharmacological, therapeutic, behavioral and/or toxicological response of the subject to the dosage form. These responses can be determined easily by those of ordinary skill in the art by monitoring the occurrence of side effects associated with the therapy, monitoring blood levels of active agent, correlating blood levels of active agent to particular formulations or patient profile, and/or observing improvement of symptoms.

The method of the invention can be adapted as follows. For frail elderly patients, lower dosages of active agent are generally required. For patients that respond poorly to a particular active agent, i.e., receive a minimal therapeutic benefit from therapy, higher dosages will be required. For patients who exhibit side effects caused by the side effect, lower dosage will be required. For patients whose eating habits interfere with drug therapy, dosages can be adjusted according to observed plasma drug concentrations to provide the desired concentrations, i.e., undesirably low plasma drug concentrations are overcome by administering higher dosages of drug. If one particular embodiment of the invention is practiced on a mammal and unwanted side effects due to high plasma drug concentrations are observed, the system can be modified by changing the formulation(s) used such that the plasma level concentrations of the drugs are lower.

The advantages of the present dosage form over known systems for treating diseases, illnesses, symptoms, or conditions can include improved therapeutic benefit and/or reduced severity or occurrence of side effects.

The following examples should not be considered exhaustive, but merely illustrative of only a few of the many embodiments contemplated by the present invention. The methods described herein can be followed to prepare osmotic devices according to the invention.

Example 1

The following procedure is used to prepare osmotic device formulations containing oxybutynin (2.5, 5 and 10 mg strength) and tolterodine (1 and 2 mg strength). The oxybutynin and the tolterodine are located in separate stacked layers in the core of the osmotic device. The osmotic device formulations contain the following ingredients in the amounts indicated:

| INGREDIENT | AMOUNT (mg) | AMOUNT (mg) | AMOUNT (mg) | AMOUNT (mg) |
|---|---|---|---|---|
| Oxybutynin Strength⇒ | 5 | 5 | 10 | 2.5 |
| Tolterodine Strength⇒ | 1 | 2 | 2 | 2 |
| CORE | | | | |
| LAYER A | | | | |
| Oxybutynin Hydrochloride | 5.15 | 5.15 | 10.30 | 2.57 |
| Mannitol | 69.00 | 69.00 | 138.00 | 50.00 |
| Anhydrous Dextrose | 30.00 | 30.00 | 60.00 | 22.00 |
| Povidone | 6.35 | 6.35 | 12.70 | 15.30 |
| Polyethylene Glycol 400 | 1.15 | 1.15 | 2.30 | 1.23 |
| Polyethylene Glycol 6000 | 4.00 | 4.00 | 8.00 | 4.00 |
| Tartaric Acid | 2.00 | 2.00 | 4.00 | 2.20 |
| Magnesium Stearate | 1.35 | 1.35 | 2.70 | 1.70 |
| Colloidal Silicon Dioxide | 1.00 | 1.00 | 2.00 | 1.00 |
| LAYER B | | | | |
| Tolterodine L-Tartrate | 1.46 | 2.92 | 2.92 | 2.92 |
| Sodium Chloride | 50.00 | 50.00 | 50.00 | 50.00 |
| Microcrystalline cellulose | 78.54 | 77.08 | 77.08 | 77.08 |
| Povidone | 9.00 | 9.00 | 9.00 | 9.00 |
| Polyethylene Glycol 6000 | 5.00 | 5.00 | 5.00 | 5.00 |
| Polyethylene Glycol 400 | 2.00 | 2.00 | 2.00 | 2.00 |
| Red Ferric Oxide | 1.00 | 1.00 | 1.00 | 1.00 |
| Colloidal Silicon Dioxide | 1.00 | 1.00 | 1.00 | 1.00 |
| Magnesium Stearate | 2.00 | 2.00 | 2.00 | 2.00 |
| COATING A | | | | |
| Cellulose Acetate | 19.05 | 19.05 | 23.75 | 23.75 |
| Polyethylene Glycol 400 | 0.95 | 0.95 | 1.25 | 1.25 |
| COATING B | | | | |
| Hydroxypropyl methylcellulose 2910 | 3.70 | 3.70 | 5.55 | 5.55 |
| Copolyvidone | 3.00 | 3.00 | 1.58 | 1.58 |
| Polyethylene Glycol 6000 | 1.05 | 1.05 | 4.50 | 4.50 |
| Titanium Dioxide | 2.25 | 2.25 | 3.37 | 3.37 |

The oxybutynin composition is prepared by mixing oxybutynin HCl, povidone, mannitol, and anhydrous dextrose. The mixture is wet with a blend of polyethylene glycol 6000 and polyethylene glycol 400 in alcohol 96°. The blend is granulated and dried at 40-50° C. for 4 hours; then, it is screened and mixed with colloidal silicon dioxide and tartaric acid. The blend is mixed to homogeneity and magnesium stearate is added.

The tolterodine composition is prepared by mixing tolterodine L-tartrate sodium chloride, povidone, microcrystalline cellulose and red ferric oxide. The mixture is wet with a blend of polyethylene glycol 6000, and polyethylene glycol 400 in alcohol 96°. The blend is granulated and dried at 40-50° C. for 4 hours; then, it is screened and mixed with colloidal silicon dioxide. The blend is mixed to homogeneity and magnesium stearate is added.

The stacked core is prepared as follows. First, the oxybutynin composition is added to a punch die set, and tamped. Next, the tolterodine composition is added on top of the tamped oxybutynin and the two layers compressed using 8.50 mm diameter punches to form bi-layered cores.

A first composition to cover the core is prepared as follows: a mixture of cellulose acetate and polyethylene glycol 400 is added to a blend of acetone and methanol. This polymer mixture is sprayed onto the tablets in a conventional pan coater to obtain film-coated tablets.

The second coating is prepared by mixing hydroxypropyl methylcellulose 2910, polyethylene glycol 6000, copolyvidone, and titanium dioxide in a mixture of methylene chloride-alcohol 96° 70:30 (volume/volume). This polymer mixture is sprayed onto the final tablets in a conventional pan coater to obtain film-coated tablets. A 0.50 mm hole is drilled through the coating in each face of the tablet.

Example 2

The procedure of Example 1 is used to prepare osmotic device formulations containing oxybutynin (5 and 10 mg strength) and darifenacin (5 and 10 mg strength) except that the formulations contain the following ingredients in the amounts indicated.

| INGREDIENT | AMOUNT(mg) | AMOUNT(mg) |
|---|---|---|
| Oxybutynin Strength ⇒ | 5 | 10 |
| Darifenacin Strength⇒ | 10 | 5 |
| CORE | | |
| LAYER A | | |
| Oxybutynin Hydrochloride | 5.15 | 10.30 |
| Mannitol | 69.00 | 138.00 |
| Anhydrous Dextrose | 30.00 | 60.00 |
| Povidone | 6.35 | 12.70 |
| Polyethylene Glycol 400 | 1.15 | 2.30 |
| Polyethylene Glycol 6000 | 4.00 | 8.00 |
| Tartaric Acid | 2.00 | 4.00 |
| Magnesium Stearate | 1.35 | 2.70 |
| Colloidal Silicon Dioxide | 1.00 | 2.00 |
| LAYER B | | |
| Darifenacin Hydrobromide | 11.90 | 5.95 |
| Sodium Chloride | 52.00 | 98.05 |
| Microcrystalline cellulose | 76.10 | 68.00 |
| Povidone | 9.00 | 16.00 |
| Polyethylene Glycol 6000 | 5.00 | 5.50 |
| Polyethylene Glycol 400 | 2.00 | 4.00 |
| Red Ferric Oxide | 1.00 | 0.50 |
| Colloidal Silicon Dioxide | 1.00 | 1.00 |
| Magnesium Stearate | 2.00 | 1.00 |
| COATING A | | |
| Cellulose Acetate | 18.50 | 33.75 |
| Polyethylene Glycol 400 | 1.50 | 1.25 |
| COATING B | | |
| Hydroxypropyl methylcellulose 2910 | 3.70 | 5.55 |
| Copolyvidone | 3.00 | 1.58 |
| Polyethylene Glycol 6000 | 1.05 | 4.50 |
| Titanium Dioxide | 2.25 | 3.37 |

Example 3

Bi-Layered Controlled Release Uncoated Tablet

These uncoated tablets provide a sustained delivery of oxybutynin and tolterodine for a period of at least about 7 hours.

| INGREDIENT | AMOUNT (mg) | AMOUNT (mg) |
|---|---|---|
| Oxybutynin Strength ⇒ | 5 | 10 |
| Tolterodine Strength ⇒ | 2 | 2 |
| LAYER A | | |
| Oxybutynin Hydrochloride | 5.15 | 10.30 |
| Myvacet 5-07 | 10.80 | 10.80 |
| Povidone K25 | 5.40 | 5.40 |
| Microcrystalline Cellulose Spheres | 68.68 | 63.53 |
| Cellulose Acetophtalate | 4.10 | 4.10 |
| Colloidal Silicon Dioxide | 0.60 | 0.60 |
| Croscarmellose Sodium | 1.80 | 1.80 |
| Magnesium Stearate | 10.80 | 10.80 |
| LAYER B | | |
| Tolterodine L-tartrate | 2.92 | 2.92 |
| Myvaplex 600P NF | 82.07 | 82.07 |
| Red Iron Oxide | 0.15 | 0.15 |
| Microcrystalline Cellulose Spheres | 67.76 | 67.76 |
| Cellulose Acetophtalate | 4.10 | 4.10 |
| Colloidal Silicon Dioxide | 0.60 | 0.60 |
| Croscarmellose Sodium | 1.80 | 1.80 |
| Magnesium Stearate | 0.75 | 0.75 |

The oxybutynin composition is prepared as follows. Myvacet 5-07 is dissolved along with oxybutynin HCl and PVP K 25. This mixture is then applied onto microcrystalline cellulose spheres. These microgranules are coated with a coat comprising cellulose acetophtalate.

The tolterodine composition is prepared as follows. Myvaplex 600P NF is hot melted in an appropriate reactor supplied with a heating chamber along with red iron oxide. Tolterodine L-tartrate is added and thoroughly mixed. This mixture is then applied on microcrystalline cellulose spheres. Next, these microgranules are coated with a coat comprising cellulose acetophthalate.

Both compositions are thoroughly mixed with colloidal silicon dioxide, croscarmellose and magnesium stearate and compressed in a suitable rotary tablet machine to make bi-layered uncoated tablets. The tablets can be coated according to Example 1 to form a dual controlled release dosage form according to the invention.

Example 4

Oxybutynin-Darifenacin Osmotic Device

The procedure of Example 1 is used to prepare osmotic device formulations containing oxybutynin (5 and 10 mg strength) and darifenacin (5 and 10 mg strength) except that the formulations contain the following ingredients in the amounts indicated.

| INGREDIENT | AMOUNT (mg) | AMOUNT (mg) |
|---|---|---|
| Oxybutynin Strength ⇒ | 5 | 10 |
| Darifenacin Strength ⇒ | 10 | 5 |
| CORE | | |
| LAYER A | | |
| Oxybutynin Hydrochloride | 5.15 | 10.30 |
| Mannitol | 69.00 | 138.00 |
| Anhydrous Dextrose | 30.00 | 60.00 |
| Povidone | 6.35 | 12.70 |
| Polyethylene Glycol 400 | 1.15 | 2.30 |
| Polyethylene Glycol 6000 | 4.00 | 8.00 |
| Tartaric Acid | 2.00 | 4.00 |
| Magnesium Stearate | 1.35 | 2.70 |
| Colloidal Silicon Dioxide | 1.00 | 2.00 |
| LAYER B | | |
| Darifenacin Hydrobromide | 11.90 | 5.95 |
| Hydroxypropylmethylcellulose 2208 (4,000) | 91.20 | 173.28 |
| Cellactose | 53.15 | 117.27 |
| Magnesium Stearate | 2.50 | 5.00 |
| Colloidal Silicon Dioxide | 1.25 | 2.50 |
| COATING A | | |
| Cellulose Acetate | 18.50 | 33.75 |
| Polyethylene Glycol 400 | 1.50 | 1.25 |
| COATING B | | |
| Hydroxypropylmethylcellulose 2910 | 3.70 | 5.55 |
| Copolyvidone | 3.00 | 1.58 |
| Polyethylene Glycol 6000 | 1.05 | 4.50 |
| Titanium Dioxide | 2.25 | 3.37 |

Additional exemplary formulations for the dosage form (1) are detailed in Examples 5 and 8. In Example 5, the dosage form is an osmotic device that comprises a tramadol-containing layer (4) in stacked arrangement with respect to the rofecoxib-containing layer (6). The core is enveloped by a wall (3) having at least two preformed passageways (5, 7). The passageway (5) is in communication with the tramadol-containing layer (4), and the passageway (7) is in communication with the rofecoxib-containing layer (6). In Example 8, the dosage form is an osmotic device that comprises a nisoldipine-containing layer (4) in stacked arrangement with respect to the captopril-containing layer (6). The core is enveloped by a wall (3) having at least one preformed passageways (7). The passageway (7) is in communication with the captopril-containing layer (6).

Example 5

The following procedure is used to prepare dual release bi-layered core osmotic device tablets containing tramadol (200 mg strength) and rofecoxib (25 mg strength). The tramadol and the rofecoxib are located in stacked layers in the core of the osmotic device, wherein the layers are in intimate contact to each other. A first passageway is in communication with the tramadol composition and a second passageway is in communication with the rofecoxib composition. The osmotic device formulations contain the following ingredients in the amounts indicated:

| INGREDIENT | AMOUNT (mg) |
|---|---|
| Tramadol Strength ⇒ | 200 |
| Rofecoxib Strength ⇒ | 25 |
| CORE | |
| LAYER A | |
| Tramadol Hydrochloride | 277.68 |
| Microcrystalline cellulose | 40.82 |

-continued

| INGREDIENT | AMOUNT (mg) |
|---|---|
| Mannitol | 26.00 |
| Polyethylene Glycol 400 | 4.00 |
| Povidone K-30 | 10.00 |
| Colloidal Silicon Dioxide | 2.00 |
| Magnesium Stearate | 3.00 |
| Purified water | 20.00 |
| LAYER B | |
| Rofecoxib | 25.00 |
| Microcrystalline cellulose | 20.00 |
| Red Ferric Oxide | 1.00 |
| Sodium Chloride | 40.00 |
| Polyox WSR 205 (MW: 600.000) | 30.00 |
| Hydroxypropyl methylcelullose 2208 (4000 cps) | 4.00 |
| Polyethylene Glycol 400 | 2.00 |
| Povidone K-30 | 10.00 |
| Colloidal Silicon Dioxide | 1.50 |
| Magnesium Stearate | 3.00 |
| Purified water | 30.00 |
| COATING A | |
| Cellulose Acetate | 19.00 |
| Polyethylene Glycol 400 | 1.00 |
| Acetone | 700.00 |
| Methanol | 300.00 |
| COATING B | |
| Opadry Y 1 18 128 A White | 10.00 |
| Purified water | 100.00 |

The tramadol HCl (200 mg) and rofecoxib (25 mg) containing tablets are prepared as follows. 277.68 g of tramadol HCl, 26.00 g of mannitol, and 40.82 g of microcrystalline cellulose are mixed for 10 minutes. The mixture is wetted with a blend of 20.00 g of purified water, 4.00 g of polyethylene glycol 400 and 10.00 g of Povidone K-30. The blend is granulated and dried at 40-50° C. for 4 hours; then, it is screened and mixed with 2.00 g of Colloidal Silicon Dioxide. The blend is mixed to homogeneity and 3.00 g of magnesium stearate is added to form a first composition.

A second granulate is prepared by mixing 25.00 g of rofecoxib, 20.00 g of microcrystalline cellulose, 1.00 g of red ferric oxide, 40.00 g of sodium chloride, 30.00 g of Polyox 205, and 4.00 g of hydroxypropyl methylcelullose 2208, for 10 minutes. The mixture is wetted with a blend of 30.00 g of purified water, 2.00 g of polyethylene glycol 400 and 10.00 g of Povidone K-30. The blend is granulated and dried at 40-50° C. for 4 hours in an oven; then, it is screened and mixed with 1.50 g of colloidal silicon dioxide. The blend is mixed to homogenize and 3.00 g of magnesium stearate is added to form a second composition.

The tramadol composition and rofecoxib composition is formed into a bi-layered core as follows: first, 363.50 mg of the tramadol composition is added to a punch die set, and tamped. Then, 136.50 mg of the rofecoxib composition is added and both layers are compressed using 10.50 mm diameter punches to obtain bi-layered uncoated cores.

The semipermeable membrane composition is prepared as follows: 19.00 g of cellulose acetate and 1.00 g of polyethylene glycol 400 in a mixture of acetone-methanol 70:30 v/v (volume/volume). This polymer mixture is sprayed onto the bi-layered uncoated cores in a perforated pan coater to obtain film-coated cores. A 0.50-mm hole is drilled through the coating on each active face of the film-coated cores to obtain perforated osmotic cores having two opposing preformed passageways.

A color coating is prepared by mixing 10.00 g of Opadry in purified water. This polymer mixture is sprayed onto the osmotic cores in a perforated pan coater to obtain the osmotic device tablets.

Example 6

The following procedure is used to prepare dual release bi-layered core osmotic device tablets containing duloxetine HCl (20 mg strength) and alprazolam (1 mg strength). The duloxetine and the alprazolam are located in separate concentric layers in the core of the osmotic device, wherein an inner layer comprises duloxetine HCl and a layer that surrounds and is in intimate contact with the inner layer comprises alprazolam. A passageway is in communication with the alprazolam composition. The osmotic device formulations contain the following ingredients in the amounts indicated:

| INGREDIENT | AMOUNT (mg) |
|---|---|
| Duloxetine Strength ⇒ | 20 |
| Alprazolam Strength ⇒ | 1 |
| CORE | |
| LAYER A | |
| Duloxetine hydrochloride | 22.40 |
| Sodium Chloride | 49.10 |
| Microcrystalline cellulose | 60.00 |
| Povidone K-30 | 7.00 |
| Polyethylene Glycol 400 | 2.00 |
| Colloidal Silicon Dioxide | 1.50 |
| Magnesium Stearate | 2.00 |
| Purified water | 20.00 |
| LAYER B | |
| Alprazolam | 1.00 |
| Microcrystalline cellulose | 90.00 |
| Red Ferric Oxide | 1.00 |
| Sodium Chloride | 20.00 |
| Polyox WSR 205 (MW: 600.000) | 30.00 |
| Hydroxypropyl methylcelullose 2208 (4000 cps) | 2.00 |
| Polyethylene Glycol 400 | 1.00 |
| Povidone K-30 | 8.00 |
| Colloidal Silicon Dioxide | 1.00 |
| Magnesium Stearate | 2.00 |
| Purified water | 30.00 |
| COATING A | |
| Cellulose Acetate | 14.25 |
| Polyethylene Glycol 400 | 0.75 |
| Acetone | 560.00 |
| Methanol | 240.00 |
| COATING B | |
| Cellulose acetate phthalate | 6.43 |
| Triacetin | 2.50 |
| Polysorbate 80 | 0.07 |
| Titanium Dioxide | 1.00 |
| Purified water | 68.00 |

The duloxetine HCl (20 mg) and alprazolam (1 mg) containing tablets are prepared as follows. 22.40 g of duloxetine HCl, 49.10 g of sodium chloride, and 60.00 g of microcrystalline cellulose are mixed. The mixture is wetted with a blend of 20.00 g of purified water, 2.00 g of polyethylene glycol 400 and 7.00 g of Povidone K-30. The blend is granulated and dried at 40-50° C. for 4 hours in an oven, then it is screened and mixed with 1.50 g of colloidal silicon dioxide. The blend is mixed to homogeneity and 2.00 g of magnesium stearate is added. The final blend is tabletted using biconcave 6.00 mm diameter punches to obtain the inner layer (inner nucleus) of the core.

A second granulate is prepared by mixing 1.00 g of alprazolam, 90.00 g of microcrystalline cellulose, 1.00 g of red ferric oxide, 20.00 g of sodium chloride, 30.00 g of Polyox 205, and 2.00 g of hydroxypropyl methylcellulose 2208. The mixture is wetted with a blend of 30.00 g of purified water, 1.00 g of polyethylene glycol 400 and 8.00 g of Povidone K-30. The blend is granulated and dried at 40-50° C. for 4 hours in an oven, then it is screened and mixed with 1.00 g of colloidal silicon dioxide. The blend is mixed to homogeneity and 2.00 g of magnesium stearate is added to form a second composition. The second composition is compressed around the first composition using a tablet press equipped with biconcave 9.00 mm diameter punches to obtain the uncoated bi-layered cores.

The semipermeable membrane composition is prepared by adding 14.25 g of cellulose acetate and 0.75 g of polyethylene glycol 400 to a mixture of acetone-methanol 70:30 v/v (volume/volume). This polymer mixture is sprayed onto the uncoated cores in a perforated pan coater to obtain film-coated cores. A 0.50-mm hole is drilled through the coating of the film-coated cores to obtain perforated coated cores.

An enteric coating is prepared by mixing cellulose acetate phthalate, triacetin, polysorbate 80 and titanium dioxide in purified water. This polymer mixture is sprayed onto the perforated coated cores in a perforated pan coater to obtain the osmotic device tablets.

Example 7

The following procedure is used to prepare dual release bi-layered core osmotic device tablets containing atorvastatin calcium 20 mg strength) and pioglitazone hydrochloride (30 mg strength). The atorvastatin and the pioglitazone are located in separate concentric layers in the core of the osmotic device, wherein an inner layer (an inner nucleus) comprises atorvastatin hydrochloride and a layer that surrounds and is in intimate contact with the inner layer and comprises pioglitazone hydrochloride. A passageway is in communication with the pioglitazone composition. The osmotic device formulations contain the following ingredients in the amounts indicated:

| INGREDIENT | AMOUNT (mg) |
| --- | --- |
| Atorvastatin Strength ⇒ | 20 |
| Pioglitazone Strength ⇒ | 30 |
| CORE | |
| LAYER A | |
| Atorvastatin calcium | 21.69 |
| Microcrystalline cellulose | 22.81 |
| Red Ferric Oxide | 1.00 |
| Sodium Chloride | 10.00 |
| Polyox WSR 205 (MW: 600.000) | 30.00 |
| Hydroxypropyl methylcellulose 2208 (4000 cps) | 5.00 |
| Polyethylene Glycol 400 | 2.00 |
| Povidone K-30 | 5.00 |
| Colloidal Silicon Dioxide | 1.00 |
| Magnesium Stearate | 1.50 |
| Purified water | 20.00 |
| LAYER B | |
| Pioglitazone HCL | 33.07 |
| Mannitol | 50.00 |
| Microcrystalline cellulose | 126.93 |
| Povidone K-30 | 5.00 |
| Polyethylene Glycol 400 | 2.00 |
| Colloidal Silicon Dioxide | 1.00 |

-continued

| INGREDIENT | AMOUNT (mg) |
| --- | --- |
| Magnesium Stearate | 2.00 |
| Purified water | 35.00 |
| COATING A | |
| Cellulose Acetate | 23.75 |
| Polyethylene Glycol 400 | 1.25 |
| Acetone | 700.00 |
| Methanol | 300.00 |
| COATING B | |
| Opadry Y 1 | 10.00 |
| Purified water | 100.00 |

The atorvastatin calcium (20 mg) and pioglitazone HCl (30 mg) tablets are prepared as follows. 21.69 g of atorvastatin calcium, 10.00 g of sodium chloride, 1.00 g of red ferric oxide, 30.00 g of Polyox 205, 5.00 g of hydroxypropyl methylcellulose 2208 and 22.81 g of microcrystalline cellulose are mixed. The mixture is wetted with a blend of 20.00 g of purified water, 2.00 g of polyethylene glycol 400 and 5.00 g of Povidone K-30. The blend is granulated and dried at 40-50° C. for 4 hours in an oven; then, it is screened and mixed with 1.00 g of colloidal silicon dioxide. The blend is mixed to homogeneity and 1.50 g of magnesium stearate is added. The final blend is tabletted using biconcave 6.00 mm diameter punches to obtain the inner nucleus of the core.

A second granulate is prepared by mixing 33.07 g of pioglitazone HCl, 126.93 g of microcrystalline cellulose and 50.00 g of mannitol. The mixture is wetted with a blend of 35.00 g of purified water, 2.00 g of polyethylene glycol 400 and 5.00 g of Povidone K-30. The blend is granulated and dried at 40-50° C. for 4 hours in an oven; then, it is screened and mixed with 1.00 g of colloidal silicon dioxide. The blend is mixed to homogenize and 2.00 g of magnesium stearate is added to form a second composition. The second composition is compressed around the inner nucleus using a tablet press equipped with biconcave 10.00 mm diameter punches. The second composition surrounds the inner layer of core to form the uncoated bi-layered cores.

The semipermeable membrane composition is prepared by adding 23.75 g of cellulose acetate and 1.25 g of polyethylene glycol 400 to a mixture of acetone-methanol 70:30 v/v (volume/volume). This polymer mixture is sprayed onto the uncoated core in a perforated pan coater to obtain film-coated cores. A 0.50-mm hole is drilled through the coating of the film-coated cores to obtain perforated osmotic cores.

A color coating is prepared by mixing 10.00 g of Opadry in purified water. This polymer mixture is sprayed onto the perforated osmotic cores in a perforated pan coater to obtain the osmotic device tablets.

Example 8

The following procedure is used to prepare osmotic device tablets containing nisoldipine (30 mg strength) and captopril (50 mg strength). The nisoldipine and the captopril are located in adjacent stacked layers in the core of the osmotic device, wherein the layers are in intimate contact to each other. A passageway is in communication with the captopril composition. The osmotic device formulations contain the following ingredients in the amounts indicated:

| INGREDIENT | AMOUNT (mg) |
| --- | --- |
| Nisoldipine Strength ⇒ | 30 |
| Captopril Strength ⇒ | 50 |
| CORE | |
| LAYER A | |
| Nisoldipine | 30.00 |
| Microcrystalline cellulose | 21.50 |
| Red Ferric Oxide | 1.00 |
| Sodium Chloride | 40.00 |
| Polyox WSR 205 (MW: 600.000) | 20.00 |
| Hydroxypropyl methylcellulose 2208 (4000 cps) | 3.00 |
| Polyethylene Glycol 400 | 2.00 |
| Povidone K-30 | 6.00 |
| Colloidal Silicon Dioxide | 1.00 |
| Magnesium Stearate | 2.50 |
| Purified water | 20.00 |
| LAYER B | |
| Captopril | 50.00 |
| Mannitol | 40.00 |
| Microcrystalline cellulose | 19.00 |
| Povidone K-30 | 8.00 |
| Polyethylene Glycol 400 | 2.00 |
| Colloidal Silicon Dioxide | 1.50 |
| Magnesium Stearate | 2.50 |
| Purified water | 25.00 |
| COATING A | |
| Cellulose Acetate | 23.75 |
| Polyethylene Glycol 400 | 1.25 |
| Acetone | 700.00 |
| Methanol | 300.00 |
| COATING B | |
| Opadry Y 1 | 10.00 |
| Purified water | 100.00 |

A large-scale batch of nisoldipine (30 mg strength) and captopril (50 mg strength). tablets is prepared by mixing 50.00 g of captopril, 40.00 g of mannitol and 19.00 g of microcrystalline cellulose. The mixture is wetted with a blend of 25.00 g of purified water, 2.00 g of polyethylene glycol 400 and 8.00 g of Povidone K-30. The blend is granulated and dried at 40-50° C. for 4 hours; then, it is screened and mixed with 1.50 g of colloidal silicon dioxide. The blend is mixed to homogeneity and 2.50 g of magnesium stearate is added to form a first composition.

A second granulate is prepared by mixing 30.00 g of nisoldipine, 21.50 g of microcrystalline cellulose, 1.00 g of red ferric oxide, 40.00 g of sodium chloride, 20.00 g of Polyox 205, and 3.00 g of hydroxypropyl methylcellulose 2208. The mixture is wetted with a blend of 20.00 g of purified water, 2.00 g of polyethylene glycol 400 and 6.00 g of Povidone K-30. The blend is granulated and dried at 40-50° C. for 4 hours in an oven; then, it is screened and mixed with 1.00 g of colloidal silicon dioxide, previously screened through a 60 mesh screen and The blend is mixed to homogeneity and 2.50 g of magnesium stearate is added.

The captopril and nisoldipine compositions are formed into a bi-layered tablet as follows: first, 123.00 mg of the captopril composition is added to a punch die set, and tamped. Then, 125.00 mg of the nisoldipine composition is added and both layers are compressed using 8.00 mm diameter punches to obtain bi-layered uncoated cores.

The semipermeable membrane composition is prepared by adding 23.75 g of cellulose acetate and 1.25 g of polyethylene glycol 400 to a mixture of acetone-methanol 70:30 v/v (volume/volume). This polymer mixture is sprayed onto the bi-layered uncoated cores in a perforated pan coater to obtain film-coated cores. A 0.50-mm hole is drilled through the coating of the captopril face of the film-coated cores to obtain perforated osmotic cores.

A color coating is prepared by mixing 10.00 g of Opadry in purified water. This polymer mixture is sprayed onto the perforated osmotic cores in a perforated pan coater to obtain the osmotic device tablets.

Example 9

The following procedure is used to prepare osmotic device tablets containing chlorpromazine HCl (200 mg strength) and levetiracetam (500 mg strength). The chlorpromazine and the levetiracetam are located in adjacent stacked layers in the core of the osmotic device, wherein the layers are in intimate contact to each other. A first passageway is in communication with the chlorpromazine composition and a second passageway is in communication with the levetiracetam composition. The osmotic device formulations contain the following ingredients in the amounts indicated:

| INGREDIENT | AMOUNT (mg) |
| --- | --- |
| Chlorpromazine HCl Strength ⇒ | 200 |
| levetiracetam Strength⇒ | 500 |
| CORE | |
| LAYER A | |
| Chlorpromazine HCl | 200.00 |
| Mannitol | 30.00 |
| Microcrystalline Cellulose | 35.00 |
| Polyethylene Glycol 400 | 0.50 |
| Povidone K-30 | 10.00 |
| Colloidal Silicon Dioxide | 1.50 |
| Magnesium Stearate | 3.00 |
| Ethanol | 40.00 |
| LAYER B | |
| Levetiracetam | 500.00 |
| Dextrose | 95.50 |
| Povidone K-30 | 15.00 |
| Polyethylene Glycol 400 | 2.00 |
| Red Ferric oxide | 1.50 |
| Colloidal Silicon Dioxide | 2.00 |
| Magnesium Stearate | 4.00 |
| Ethanol | 50.00 |
| COATING A | |
| Cellulose Acetate | 29.50 |
| Polyethylene Glycol 400 | 1.60 |
| Acetone | 1086.80 |
| Methanol | 465.80 |
| COATING B | |
| Opadry Y 1 18 128 A White | 15.50 |
| Purified water | 100.00 |

The chlorpromazine HCl (200 mg) and levetiracetam (500 mg) containing tablets are prepared as follows. 200.00 g of chlorpromazine HCl, 30.00 g of mannitol, and 35.00 g of microcrystalline cellulose are mixed for 10 minutes. The mixture is wetted with a blend of 40.00 g of ethanol, 0.50 g of polyethylene glycol 400, and 10.00 g of Povidone K-30. The blend is granulated and dried at 40-50° C. for 4 hours; then, it is screened and mixed with 1.50 g of colloidal silicon dioxide, previously screened through a 60 mesh screen, and 3.00 g of magnesium stearate, previously screened through a 60 mesh screen, to form a first composition.

A second granulate is prepared by mixing 500.00 g of levetiracetam, 95.50 g of dextrose, 1.50 g of red ferric oxide, and 1.00 g of colloidal silicon dioxide, for 10 minutes. The mixture is wetted with a blend of 50.00 g of ethanol, 2.00 g of polyethylene glycol 400 and 15.00 g of Povidone K-30. The blend is granulated and dried at 40-50° C. for 4 hours in an oven; then, it is screened and mixed with 1.00 g of colloidal silicon dioxide, previously screened through a 60 mesh screen, and 4.00 g of magnesium stearate, previously screened through a 60 mesh screen, to form a second composition.

The chlorpromazine HCl composition and the levetiracetam composition are formed into a bi-layered core as follows: first, 280.00 mg of the chlorpromazine composition is added to a punch die set, and tamped. Then, 620.00 mg of the levetiracetam composition is added and both layers are compressed using 14.00 mm diameter punches to obtain bi-layered uncoated cores.

The semipermeable membrane composition is prepared as follows: 29.50 g of cellulose acetate and 1.60 g of polyethylene glycol 400 in a mixture of acetone-methanol 70:30 v/v (volume/volume). This polymer mixture is sprayed onto the bi-layered uncoated cores in a perforated pan coater to obtain film-coated cores. A 0.50-mm hole is drilled through the coating on each active face of the film-coated cores to obtain perforated osmotic cores having two opposing preformed passageways.

A color coating is prepared by mixing 15.50 g of Opadry in purified water. This polymer mixture is sprayed onto the osmotic cores in a perforated pan coater to obtain the osmotic device tablets.

Those of skill in the art should, in light of the present disclosure, appreciate that many changes can be made in the specific embodiments that are disclosed herein and still obtain a like or similar result without departing from the spirit and scope of the invention. All of the compositions and methods disclosed and claimed herein can be made and executed without undue experimentation in light of the present disclosure.

We claim:

1. A dual controlled release osmotic device consisting essentially of:
    a bi-layered core consisting essentially of a controlled release active agent-containing first layer and a controlled release active agent-containing second layer, wherein the first and second layers are in intimate contact with one another and in stacked arrangement, and the osmotic device excludes a partition between the first layer and the second layer and excludes a push-layer; and
    a membrane enveloping the core, wherein the membrane comprises at least one preformed passageway in communication with at least one of the first and second active agent-containing layers;
    whereby the osmotic device provides a controlled release of the first active agent through at least one preformed passageway according to a first release profile and the second layer provides a controlled release of the second active agent through at least one preformed passageway according to a second release profile, and
    wherein the first and second active agents are independently selected at each occurrence from the group consisting of an antibiotic agent, antihistamine agent, decongestant, anti-inflammatory agent, antiparasitic agent, antiviral agent, local anesthetic, antifungal agent, amoebicidal agent, trichomonocidal agent, analgesic agent, anti-arthritic agent, anti-asthmatic agent, anticoagulant agent, anticonvulsant agent, anti-Alzheimer's disease agent antidepressant agent, antidiabetic agent, antineoplastic agent, anti-psychotic agent, neuroleptic agent, antihypertensive agent, hypnotic agent, sedative agent, anxiolytic energizer agent, anti-Parkinson agent, muscle relaxant agent, antimalarial agent, hormonal agent, contraceptive agent, sympathomimetic agent, hypoglycemic agent, antilipemic agent, ophthalmic agent, electrolytic agent, diagnostic agent, prokinetic agent, gastric acid secretion inhibitor agent, anti-ulcerant agent, anti-flatulent agent, anti-incontinence agent, and cardiovascular agent.

2. The osmotic device of claim 1, wherein the osmotic device comprises at least one first preformed passageway in communication with the first layer and at least one second preformed passageway in communication with the second layer.

3. The osmotic device of claim 2, wherein at least one of the two preformed passageways is plugged with a water soluble and/or water erodible material.

4. The osmotic device of claim 2, wherein both of the preformed passageways are plugged with a water soluble and/or water erodible material, and the material plugging the first passageway is the same as the material plugging the second passageway.

5. The osmotic device of claim 2, wherein both of the preformed passageways are plugged with a water soluble and/or water erodible material, and the material plugging the first passageway is different than the material plugging the second passageway.

6. The osmotic device of claim 1, wherein the membrane comprises at least one preformed passageway in communication with both the first and second layers.

7. The osmotic device of claim 1 further comprising at least one external coat exterior to the membrane.

8. The osmotic device of claim 7, wherein the external coat is independently selected at each occurrence from water soluble and/or water erodible.

9. The osmotic device of claim 7, wherein the external coat is independently selected at each occurrence from microporous, permeable, semipermeable and impermeable.

10. The osmotic device of claim 7, wherein the external coat is independently selected at each occurrence from inert and drug-containing.

11. The osmotic device of claim 10, wherein the external coat provides a rapid release of drug.

12. The osmotic device of claim 7, wherein the membrane comprises at least a first preformed passageway and at least a second preformed passageway, wherein the first passageway has been formed after application of the external coat to the membrane, and the second passageway has been formed before application of the external coat to the membrane such that the second passageway is plugged by the external coat, and release of the second active agent begins after release of the first active agent has started.

13. The osmotic device of claim 7, wherein the membrane comprises at least a first preformed passageway and at least a second preformed passageway, wherein the first and second passageways have been formed before application of the external coat to the membrane; and the first and second passageways are plugged by the external coat.

14. The osmotic device of claim 1 further comprising at least one internal coat interposed the core and the membrane.

15. The osmotic device of claim 14, wherein the internal coat is independently selected at each occurrence from water soluble and/or water erodible.

16. The osmotic device of claim 14, wherein the internal coat is independently selected at each occurrence from inert and drug-containing.

17. The osmotic device of claim 14, wherein the internal coat is independently selected at each occurrence from microporous, permeable, semipermeable and impermeable.

18. The osmotic device of claim 1, wherein the first active agent and the second active agent are released from the core sequentially or in an overlapping manner when the osmotic device is exposed to an aqueous environment.

19. The osmotic device of claim 1, wherein each active agent is independently released from the core according to a timed, targeted, pseudo-first order, first order, pseudo-zero order, zero-order, sustained, slow, extended, pulsatile and/or delayed release profile.

20. The osmotic device of claim 1, wherein initial release of the first active agent and the second active agent is delayed for a period of time after exposure to an aqueous environment.

21. The osmotic device of claim 20, wherein each active agent is independently released from the core according to a timed, targeted, pseudo-first order, first order, pseudo-zero order, zero-order, sustained, slow, extended, and/or pulsatile release profile.

22. The osmotic device of claim 1 comprising:
a bi-layered core consisting essentially of a controlled release first layer comprising a first drug and at least one pharmaceutical excipient, and a different controlled release second layer comprising a second drug and at least one pharmaceutical excipient, wherein the first and second layers are in intimate contact with one another and in stacked arrangement, and the core excludes a partition between the first layer and the second layer and excludes a push-layer; and
a membrane enveloping the core and having at least two preformed passageways to permit a controlled release of the first and second drugs from the core when the osmotic device is exposed to an aqueous environment, wherein at least one first passageway is in communication with the first layer and at least one second passageway is in communication with the second layer;
wherein the first and second active drugs are independently selected at each occurrence from the group consisting of an antibiotic agent, antihistamine agent, decongestant, anti-inflammatory agent, antiparasitic agent, antiviral agent, local anesthetic, antifungal agent, amoebicidal agent, trichomonocidal agent, analgesic agent, anti-arthritic agent, anti-asthmatic agent, anticoagulant agent, anticonvulsant agent, anti-Alzheimer's disease agent antidepressant agent, antidiabetic agent, antineoplastic agent, anti-psychotic agent, neuroleptic agent, antihypertensive agent, hypnotic agent, sedative agent, anxiolytic energizer agent, anti-Parkinson agent, muscle relaxant agent, antimalarial agent, hormonal agent, contraceptive agent, sympathomimetic agent, hypoglycemic agent, antilipemic agent, ophthalmic agent, electrolytic agent, diagnostic agent, prokinetic agent, gastric acid secretion inhibitor agent, anti-ulcerant agent, anti-flatulent agent, anti-incontinence agent, and cardiovascular agent.

23. The osmotic device of claim 22, wherein the membrane is semipermeable.

24. The osmotic device of claim 22, wherein each drug is independently released from the core according to a timed, targeted, pseudo-first order, first order, pseudo-zero order, zero-order, sustained, slow, extended, pulsatile and/or delayed release profile.

25. The osmotic device of claim 22, wherein the first drug and the second drug are released from the core sequentially or in an overlapping manner when the osmotic device is exposed to an aqueous environment.

26. The osmotic device of claim 22 further comprising at least one external coat exterior to the membrane.

27. The osmotic device of claim 26, wherein the external coat is independently selected at each occurrence from water soluble and/or water erodible.

28. The osmotic device of claim 26, wherein the external coat is independently selected at each occurrence from microporous, permeable, semipermeable and impermeable.

29. The osmotic device of claim 26, wherein the external coat is independently selected at each occurrence from inert and drug-containing.

30. The osmotic device of claim 29, wherein the external coat provides a rapid release of drug.

31. The osmotic device of claim 26, wherein the first passageway has been formed after application of the external coat to the semipermeable membrane and the second passageway has been formed before application of the external coat to the semipermeable membrane such that the second passageway is plugged by the external coat and release of the second drug begins after release of the first drug has started.

32. The osmotic device of claim 26, wherein the first and second passageways have been formed before application of the external coat to the semipermeable membrane; the first and second passageways are plugged by the external coat; and release of the first drug and the second drug is delayed for a period of time after exposure to an aqueous environment.

33. The osmotic device of claim 22 further comprising at least one internal coat interposed the core and the membrane.

34. The osmotic device of claim 33, wherein the internal coat is independently selected at each occurrence from water soluble and/or water erodible.

35. The osmotic device of claim 33, wherein the internal coat is independently selected at each occurrence from inert and drug-containing.

36. The osmotic device of claim 33, wherein the internal coat is independently selected at each occurrence from microporous, permeable, semipermeable and impermeable.

37. The osmotic device of claim 22, wherein the first drug and the second drug are released sequentially or in an overlapping manner when the osmotic device is exposed to an aqueous environment.

38. The osmotic device of claim 1 comprising:
a bi-layered core consisting essentially of a controlled release first active agent-containing first layer and a controlled release second active agent-containing second layer, wherein the first and second layers are in intimate contact with one another, and the layers are in stacked arrangement, and the core excludes a partition between the first layer and the second layer and excludes a push-layer; and
a semipermeable membrane enveloping the core, wherein the membrane comprises at least one preformed passageway in communication with at least one of the first and second active agent-containing layers;
whereby the osmotic device provides a controlled release of the first active agent through at least one preformed passageway according to a first release profile and the second layer provides a controlled release of the second active through at least one preformed passageway according to a second release profile, and each drug is independently released from the core according to a timed, targeted, pseudo-first order, first order, pseudo-zero order, zero-order, sustained, slow, extended, pulsatile and/or delayed release profile;
wherein the first and second active agents are independently selected at each occurrence from the group consisting of an antibiotic agent, antihistamine agent, decongestant, anti-inflammatory agent, antiparasitic agent, antiviral agent, local anesthetic, antifungal agent, amoebicidal agent, trichomonocidal agent, analgesic agent, anti-arthritic agent, anti-asthmatic agent, anticoagulant agent, anticonvulsant agent, anti-Alzheimer's disease agent antidepressant agent, antidiabetic agent, antineoplastic agent, anti-psychotic agent, neuroleptic agent, antihypertensive agent, hypnotic agent, sedative agent, anxiolytic energizer agent, anti-Parkinson agent, muscle relaxant agent, antimalarial agent, hormonal agent, contraceptive agent, sympathomimetic agent, hypoglycemic agent, antilipemic agent, ophthalmic agent, electrolytic agent, diagnostic agent, prokinetic agent, gastric acid secretion inhibitor agent, anti-ulcerant agent, anti-flatulent agent, anti-incontinence agent, and cardiovascular agent.

39. The osmotic device of claim 38 further comprising at least one external coat exterior to the membrane.

40. The osmotic device of claim 39, wherein the external coat is independently selected at each occurrence from water soluble and/or water erodible.

41. The osmotic device of claim 39, wherein the external coat is independently selected at each occurrence from microporous, permeable, semipermeable and impermeable.

42. The osmotic device of claim 39, wherein the external coat is independently selected at each occurrence from inert and drug-containing.

43. The osmotic device of claim 42, wherein the external coat provides a rapid release of drug.

44. The osmotic device of claim 39, wherein the first passageway has been formed after application of the external coat to the semipermeable membrane and the second passageway has been formed before application of the external coat to the semipermeable membrane such that the second passageway is plugged by the external coat and release of the second active agent begins after release of the first active agent has started.

45. The osmotic device of claim 39, wherein the first and second passageways have been formed before application of the external coat to the semipermeable membrane; the first and second passageways are plugged by the external coat; and release of the first active agent and the second active agent is delayed for a period of time after exposure to an aqueous environment.

46. The osmotic device of claim 38 further comprising at least one internal coat interposed the core and the membrane.

47. The osmotic device of claim 46, wherein the internal coat is independently selected at each occurrence from water soluble and/or water erodible.

48. The osmotic device of claim 46, wherein the internal coat is independently selected at each occurrence from microporous, permeable, semipermeable and impermeable.

49. The osmotic device of claim 46, wherein the internal coat is independently selected at each occurrence from inert and drug-containing.

50. The osmotic device of claim 38, wherein the first active agent and the second active agent are released sequentially or in an overlapping manner when the osmotic device is exposed to an aqueous environment.

51. The osmotic device of claim 1, 22 or 38, wherein the first release profile and the second release profile are different.

52. The osmotic device of claim 1, wherein first and second active agents are selected as follows:
a) the first active agent is a prokinetic agent and the second active agent is a gastric acid secretion inhibitor agent;
b) the first active agent is a decongestant and the second active agent is an antihistamine;
c) the first active agent is a first anti-incontinence agent and the second active agent is a different second anti-incontinence agent;
d) the first active agent is a first antihypertensive agent and the second active agent is a different second antihypertensive agent;
e) the first active agent is an antidepressant agent and the second active agent is an anti-psychotic agent;
f) the first active agent is a first analgesic or anti-inflammatory agent, and the second active agent is a different second analgesic or anti-inflammatory agent;
g) the first active agent is an antiviral agent and the second active agent is an antihistamine agent;
h) the first active agent is a muscle relaxant agent and the second active agent is an anti-inflammatory or analgesic agent;
i) the first active agent is an antidiabetic agent and the second active agent is a different antidiabetic agent;
j) the first active agent is an antidepressant and the second active agent is an agent for the treatment of Alzheimer's disease;
k) the first active agent is an anticonvulsant and the second active agent is an anti-psychotic agent;
l) the first active agent is an antilipemic agent and the second active agent is a different antilipemic agent;
m) the first active agent is an antidepressant and the second active agent is an anti-Parkinson agent; or
n) the first active agent is an antidiabetic agent and the second active agent is an antilipemic agent.

53. The osmotic device of claim 52, wherein the first and second active agents are selected as follows:
a) the first active agent is pridinol and the second active agent is a selective or specific COX-II inhibitor agent;
b) the analgesic and anti-inflammatory agents are selected from the group consisting of an non-steroidal anti-inflammatory agent, a steroidal, anti-inflammatory agent, an opioid receptor agonist agent, and a selective or specific COX-II inhibitor agent;
c) the antihypertensive agent is selected from the group consisting of a calcium channel blocker agent, an angiotensin converting enzyme inhibitor agent, a diuretic agent and a beta-adrenergic antagonist agent;
d) the antidiabetic agent is selected from the following main groups of oral antidiabetic drugs available: sulphonylureas, tolbutamide, chlorpropamide, tolazamide, acetohexamide, glibenclamide, gliclazide, 1-butyl-3-metanilylurea, carbutamide, glibonuride, glipizide, glyburide, gliquidone, glisoxepid, glybuthiazole, glibuzole, glyhexamide, glymidine, glypinamide, phenbutamide, and tolcyclamide; thiazolidinediones, glitazones, rosiglitazone, pioglitazone, and troglitazone; biguanidines, metformin, nateglinide, and repaglinide;
e) the anti-Alzheimer's disease agent is selected from the group consisting of memantine, donepezil, galantamine, rivastigmine, and tacrine;
f) the antidepressant is selected from the group consisting of venlafaxine, amitriptyline, citalopram, bupropion, clomipramine, desipramine, nefazodone, fluoxetine, doxepin, fluvoxamine, maprotiline, imipramine, mirtazapine, nortriptyline, paroxetine, phenelzine, tranylcypromine, protriptyline, sertraline, trazodone, trimipramine, and amoxapine;
g) the anticonvulsant is selected from the group consisting of carbamazepine, lamotrigine, levetiracetam, oxcarbazepine, topiramate, and zonisamide;

h) the antipsychotic agent is selected from the group consisting of chlorpromazine, clozapine, fluphenazine, haloperidol, loxapine, mesoridazine, molindone, olanzapine, quetiapine, ziprasidone, risperidone, perphenazine, pimozide, prochlorperazine, thioridazine, thiothixene, and trifluoperazine;

i) the antilipemic agent is selected from the group consisting of cholestyramine, cholestipol, nicotinic acid, clofibrate, gemfibrozil, dextrothyroxine sodium, prabucol, mevastatin, lovastatin, simvastatin, pravastatin, fluvastatin, atorvastatin, pitavastatin, and ezetimibe;

j) the anti-Parkinson agent is selected from the group consisting of levodopa, benztropine mesylate, benzeraside, carbidopa, bromocriptine, pergolide, selegiline, ropirinol, pramipexole, amantadine, entacapone, tolcapone, biperiden, carbelogine, apomorphine, lisuride, procyclidine, and trihexylphenidyl;

k) the analgesic agent is selected from the group comprising oxycodone, hydrocodone, tramadol, and gabapentin; or l) the first active agent is pridinol and the second active agent is licofelone.

54. The osmotic device of claim 1 further comprising an osmagent, osmopolymer, adsorbent, antioxidant, buffering agent, colorant, flavorant, sweetening agent, tablet antiadherent, tablet binder, tablet diluent, capsule diluent, tablet direct compression excipient, tablet disintegrant, tablet glidant, tablet lubricant, tablet or capsule opaquant, tablet polishing agent, plasticizer, polymer, oil, fatty acid, detergent, soap, wax or combination thereof.

55. A dual controlled release osmotic device consisting essentially of:
a bi-layered core consisting essentially of a controlled release active agent-containing first layer and a controlled release active agent-containing second layer, wherein the first and second layers are in intimate contact with one another and in stacked arrangement, and the osmotic device excludes a partition between the first layer and the second layer and excludes a push-layer; and
a membrane enveloping the core, wherein the membrane comprises at least one preformed passageway in communication with at least one of the first and second active agent-containing layers;
whereby the osmotic device provides a controlled release of the first active agent through at least one preformed passageway according to a first release profile and the second layer provides a controlled release of the second active agent through at least one preformed passageway according to a second release profile,
wherein the first and second active agents are independently selected at each occurrence from the group consisting of medicine, nutrient, food product, insecticide, pesticide, herbicide, germicide, algaecide, fungicide, chemical reagent, growth regulating substance, parasiticide, sex sterilant, fertility promoter, biocide, rodenticide, disinfectant, anti-oxidant, plant growth promoter, preservative, fermentation agent, fertility inhibitor, deodorant, micro-organism attenuator, catalyst, food supplement, cosmetic and vitamin.

56. The osmotic device of claim 55, wherein the osmotic device comprises at least one first preformed passageway in communication with the first layer and at least one second preformed passageway in communication with the second layer.

57. The osmotic device of claim 56, wherein at least one of the two preformed passageways is plugged with a water soluble and/or water erodible material.

58. The osmotic device of claim 56, wherein both of the preformed passageways are plugged with a water soluble and/or water erodible material, and the material plugging the first passageway is the same as the material plugging the second passageway.

59. The osmotic device of claim 56, wherein both of the preformed passageways are plugged with a water soluble and/or water erodible material, and the material plugging the first passageway is different than the material plugging the second passageway.

60. The osmotic device of claim 55, wherein the membrane comprises at least one preformed passageway in communication with both the first and second layers.

61. The osmotic device of claim 55 further comprising at least one external coat exterior to the membrane.

62. The osmotic device of claim 61, wherein the external coat is independently selected at each occurrence from water soluble and/or water erodible.

63. The osmotic device of claim 61, wherein the external coat is independently selected at each occurrence from microporous, permeable, semipermeable and impermeable.

64. The osmotic device of claim 61, wherein the external coat is independently selected at each occurrence from inert and drug-containing.

65. The osmotic device of claim 64, wherein the external coat provides a rapid release of drug.

66. The osmotic device of claim 61, wherein the membrane comprises at least a first preformed passageway and at least a second preformed passageway, wherein the first passageway has been formed after application of the external coat to the membrane, and the second passageway has been formed before application of the external coat to the membrane such that the second passageway is plugged by the external coat, and release of the second active agent begins after release of the first active agent has started.

67. The osmotic device of claim 61, wherein the membrane comprises at least a first preformed passageway and at least a second preformed passageway, wherein the first and second passageways have been formed before application of the external coat to the membrane; and the first and second passageways are plugged by the external coat.

68. The osmotic device of claim 55 further comprising at least one internal coat interposed the core and the membrane.

69. The osmotic device of claim 68, wherein the internal coat is independently selected at each occurrence from water soluble and/or water erodible.

70. The osmotic device of claim 68, wherein the internal coat is independently selected at each occurrence from inert and drug-containing.

71. The osmotic device of claim 68, wherein the internal coat is independently selected at each occurrence from microporous, permeable, semipermeable and impermeable.

72. The osmotic device of claim 55, wherein the first active agent and the second active agent are released from the core sequentially or in an overlapping manner when the osmotic device is exposed to an aqueous environment.

73. The osmotic device of claim 55, wherein each active agent is independently released from the core according to a timed, targeted, pseudo-first order, first order, pseudo-zero order, zero-order, sustained, slow, extended, pulsatile and/or delayed release profile.

74. The osmotic device of claim 55, wherein initial release of the first active agent and the second active agent is delayed for a period of time after exposure to an aqueous environment.

75. The osmotic device of claim 74, wherein each active agent is independently released from the core according to a timed, targeted, pseudo-first order, first order, pseudo-zero order, zero-order, sustained, slow, extended, and/or pulsatile release profile.

76. The osmotic device of claim 55 comprising:
a bi-layered core consisting essentially of a controlled release first layer comprising a first drug and at least one pharmaceutical excipient, and a different controlled release second layer comprising a second drug and at least one pharmaceutical excipient, wherein the first and second layers are in intimate contact with one another and in stacked arrangement, and the core excludes a partition between the first layer and the second layer and excludes a push-layer; and
a membrane enveloping the core and having at least two preformed passageways to permit a controlled release of the first and second drugs from the core when the osmotic device is exposed to an aqueous environment, wherein at least one first passageway is in communication with the first layer and at least one second passageway is in communication with the second layer,
wherein the first and second drugs are selected from the group consisting of medicine, germicide, fungicide, growth regulating substance, parasiticide, sex sterilant, fertility promoter, biocide, anti-oxidant, fertility inhibitor and micro-organism attenuator.

77. The osmotic device of claim 76, wherein the membrane is semipermeable.

78. The osmotic device of claim 76, wherein each drug is independently released from the core according to a timed, targeted, pseudo-first order, first order, pseudo-zero order, zero-order, sustained, slow, extended, pulsatile and/or delayed release profile.

79. The osmotic device of claim 76, wherein the first drug and the second drug are released from the core sequentially or in an overlapping manner when the osmotic device is exposed to an aqueous environment.

80. The osmotic device of claim 76 further comprising at least one external coat exterior to the membrane.

81. The osmotic device of claim 80, wherein the external coat is independently selected at each occurrence from water soluble and/or water erodible.

82. The osmotic device of claim 80, wherein the external coat is independently selected at each occurrence from microporous, permeable, semipermeable and impermeable.

83. The osmotic device of claim 80, wherein the external coat is independently selected at each occurrence from inert and drug-containing.

84. The osmotic device of claim 83, wherein the external coat provides a rapid release of drug.

85. The osmotic device of claim 80, wherein the first passageway has been formed after application of the external coat to the semipermeable membrane and the second passageway has been formed before application of the external coat to the semipermeable membrane such that the second passageway is plugged by the external coat and release of the second drug begins after release of the first drug has started.

86. The osmotic device of claim 80, wherein the first and second passageways have been formed before application of the external coat to the semipermeable membrane;
the first and second passageways are plugged by the external coat; and release of the first drug and the second drug is delayed for a period of time after exposure to an aqueous environment.

87. The osmotic device of claim 76 further comprising at least one internal coat interposed the core and the membrane.

88. The osmotic device of claim 87, wherein the internal coat is independently selected at each occurrence from water soluble and/or water erodible.

89. The osmotic device of claim 87, wherein the internal coat is independently selected at each occurrence from inert and drug-containing.

90. The osmotic device of claim 87, wherein the internal coat is independently selected at each occurrence from microporous, permeable, semipermeable and impermeable.

91. The osmotic device of claim 79, wherein the first drug and the second drug are released sequentially or in an overlapping manner when the osmotic device is exposed to an aqueous environment.

92. The osmotic device of claim 55 comprising:
a bi-layered core consisting essentially of a controlled release first active agent-containing first layer and a controlled release active second agent-containing second layer, wherein the first and second layers are in intimate contact with one another, and the layers are in stacked arrangement, and the core excludes a partition between the first layer and the second layer and excludes a push-layer; and
a semipermeable membrane enveloping the core, wherein the membrane comprises at least one preformed passageway in communication with at least one of the first and second active agent-containing layers;
whereby the osmotic device provides a controlled release of the first active agent through at least one preformed passageway according to a first release profile and the second layer provides a controlled release of the second active through at least one preformed passageway according to a second release profile, and each drug is independently released from the core according to a timed, targeted, pseudo-first order, first order, pseudo-zero order, zero-order, sustained, slow, extended, pulsatile and/or delayed release profile,
wherein the first and second active agents are selected from the group consisting of medicine, nutrient, food product, insecticide, pesticide, herbicide, germicide, algaecide, fungicide, chemical reagent, growth regulating substance, parasiticide, sex sterilant, fertility promoter, biocide, rodenticide, disinfectant, anti-oxidant, plant growth promoter, preservative, fermentation agent, fertility inhibitor, deodorant, micro-organism attenuator, catalyst, food supplement, cosmetic and vitamin.

93. The osmotic device of claim 92 further comprising at least one external coat exterior to the membrane.

94. The osmotic device of claim 93, wherein the external coat is independently selected at each occurrence from water soluble and/or water erodible.

95. The osmotic device of claim 93, wherein the external coat is independently selected at each occurrence from microporous, permeable, semipermeable and impermeable.

96. The osmotic device of claim 93, wherein the external coat is independently selected at each occurrence from inert and drug-containing.

97. The osmotic device of claim 96, wherein the external coat provides a rapid release of drug.

98. The osmotic device of claim 93, wherein the first passageway has been formed after application of the external coat to the semipermeable membrane and the second passageway has been formed before application of the external coat to the semipermeable membrane such that the second passageway is plugged by the external coat and release of the second active agent begins after release of the first active agent has started.

99. The osmotic device of claim 93, wherein the first and second passageways have been formed before application of the external coat to the semipermeable membrane; the first and second passageways are plugged by the external coat; and release of the first active agent and the second active agent is delayed for a period of time after exposure to an aqueous environment.

100. The osmotic device of claim 92 further comprising at least one internal coat interposed the core and the membrane.

101. The osmotic device of claim 100, wherein the internal coat is independently selected at each occurrence from water soluble and/or water erodible.

102. The osmotic device of claim 100, wherein the internal coat is independently selected at each occurrence from microporous, permeable, semipermeable and impermeable.

103. The osmotic device of claim 100, wherein the internal coat is independently selected at each occurrence from inert and drug-containing.

104. The osmotic device of claim 92, wherein the first active agent and the second active agent are released sequentially or in an overlapping manner when the osmotic device is exposed to an aqueous environment.

105. The osmotic device of claim 55, 76 or 92, wherein the first release profile and the second release profile are different.

106. The osmotic device of claim 55 or 92, wherein: the first active agent is oxybutynin; and the second active agent is a drug for treating incontinence.

107. The osmotic device of claim 106, wherein the second active agent is selected from the group consisting of darifenacin, tolterodine, and duloxetine.

108. The osmotic device of claim 76, wherein the first drug is oxybutynin; and the second drug is a drug for treating incontinence.

109. The osmotic device of claim 108, wherein the second drug is selected from the group consisting of darifenacin, tolterodine, and duloxetine.

110. The osmotic device of claim 55, 76 or 92, wherein the core further comprises at least one pharmaceutical excipient selected from the group consisting of adsorbent, antioxidant, buffering agent, colorant, flavorant, sweetening agent, tablet antiadherent, tablet binder, tablet diluent, capsule diluent, tablet direct compression excipient, tablet disintegrant, tablet glidant, tablet lubricant, tablet opaquant, capsule opaquant, polymer, plasticizer, oil, soap, synthetic detergent and tablet polishing agent.

* * * * *